US010077291B2

(12) United States Patent
Asokan et al.

(10) Patent No.: US 10,077,291 B2
(45) Date of Patent: Sep. 18, 2018

(54) METHODS AND COMPOSITIONS FOR DUAL GLYCAN BINDING AAV VECTORS

(71) Applicant: The University of North Carolina at Chapel Hill, Chapel Hill, NC (US)

(72) Inventors: Aravind Asokan, Chapel Hill, NC (US); Richard Samulski, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 146 days.

(21) Appl. No.: 14/777,070

(22) PCT Filed: Mar. 14, 2014

(86) PCT No.: PCT/US2014/028545
§ 371 (c)(1),
(2) Date: Sep. 15, 2015

(87) PCT Pub. No.: WO2014/144229
PCT Pub. Date: Sep. 18, 2014

(65) Prior Publication Data

US 2016/0017005 A1 Jan. 21, 2016

Related U.S. Application Data

(60) Provisional application No. 61/802,111, filed on Mar. 15, 2013.

(51) Int. Cl.

| | |
|---|---|
| *C12N 7/00* | (2006.01) |
| *C12N 15/86* | (2006.01) |
| *A61K 48/00* | (2006.01) |
| *C07K 14/005* | (2006.01) |

(52) U.S. Cl.
CPC .............. *C07K 14/005* (2013.01); *C12N 7/00* (2013.01); *C12N 15/86* (2013.01); *A61K 48/00* (2013.01); *C12N 2750/14122* (2013.01); *C12N 2750/14141* (2013.01); *C12N 2750/14142* (2013.01); *C12N 2750/14171* (2013.01)

(58) Field of Classification Search
None
See application file for complete search history.

(56) References Cited

U.S. PATENT DOCUMENTS

| | | | |
|---|---|---|---|
| 4,501,729 | A | 2/1985 | Boucher et al. |
| 4,968,603 | A | 11/1990 | Slamon et al. |
| 5,399,346 | A | 3/1995 | Anderson et al. |
| 5,863,541 | A | 1/1999 | Samulski et al. |
| 5,869,248 | A | 2/1999 | Yuan et al. |
| 5,877,022 | A | 3/1999 | Stinchcomb et al. |
| 5,882,652 | A | 3/1999 | Valdes et al. |
| 5,905,040 | A | 5/1999 | Mazzara et al. |
| 5,916,563 | A | 6/1999 | Young et al. |
| 6,013,487 | A | 1/2000 | Mitchell |
| 6,040,183 | A | 3/2000 | Ferrari et al. |
| 6,083,702 | A | 7/2000 | Mitchell et al. |
| 6,093,570 | A | 7/2000 | Ferrari et al. |
| 6,156,303 | A | 12/2000 | Russell et al. |
| 7,071,172 | B2 | 7/2006 | McCown et al. |
| 7,201,898 | B2 | 4/2007 | Monahan et al. |
| 2002/0192189 | A1 | 12/2002 | Xiao et al. |
| 2003/0017131 | A1 | 1/2003 | Park et al. |
| 2004/0013645 | A1 | 1/2004 | Monahan et al. |
| 2009/0191597 | A1 | 7/2009 | Samulski et al. |

FOREIGN PATENT DOCUMENTS

| | | | |
|---|---|---|---|
| WO | WO 90/05142 | A1 | 5/1990 |
| WO | WO 98/11244 | A2 | 3/1998 |
| WO | WO 00/17377 | A2 | 3/2000 |
| WO | WO 00/28004 | A1 | 5/2000 |
| WO | WO 00/28061 | A2 | 5/2000 |
| WO | WO 01/92551 | A2 | 12/2001 |
| WO | WO 03/095647 | A2 | 11/2003 |
| WO | WO 2006/021724 | A2 | 3/2006 |
| WO | WO 2006/029319 | A2 | 3/2006 |
| WO | WO 2006/073052 | A1 | 7/2006 |
| WO | WO 2006/119137 | A1 | 11/2006 |
| WO | WO 2007/089632 | A2 | 8/2007 |
| WO | WO 2007/100465 | A2 | 9/2007 |
| WO | WO 2008/088895 | A2 | 7/2008 |
| WO | WO 2010/031865 | A1 | 3/2010 |
| WO | WO 2010/093784 | A2 | 8/2010 |
| WO | WO 2012/109570 | A1 | 8/2012 |
| WO | WO 2013/170078 | A1 | 11/2013 |

OTHER PUBLICATIONS

Agbandje-McKenna et al. "AAV Capsid Structure and Cell Interactions" *Methods in Molecular Biology* 807(Chapter 3):47-92 (2011).
Andino et al. "AAV-mediated knockdown of phospholamban leads to improved contractility and calcium handling in cardiomyocytes" *The Journal of Gene Medicine* 10:132-142 (2008).
Arnold et al. "The Swiss-Model workspace: a web-based environment for protein structure homology modelling" *Bioinformatics* 22(2):195-201 (2006).
Arruda et al. "Regional intravascular delivery of AAV-2-F.IX to skeletal muscle achieves long-term correction of hemophilia B in a large animal model" *Blood* 105(9):3458-3464 (2005).
Asokan et al. "Reengineering a receptor footprint of adeno-associated virus enables selective and systemic gene transfer to muscle" *Nature Biotechnology* 28(1):79-83 (2010).
Asokan et al. "The AAV Vector Toolkit: Poised at the Clinical Crossroads" *Molecular Therapy* 20(4):699-708 (2012).
Bantel-Schaal et al. "Human Adeno-Associated Virus Type 5 Is Only Distantly Related to Other Known Primate Helper-Dependent Parvoviruses" *Journal of Virology* 73(2):939-947 (1999).
Bell et al. "The AAV9 receptor and its modification to improve in vivo lung gene transfer in mice" *The Journal of Clinical Investigation* 121(6):2427-2435 (2011).

(Continued)

*Primary Examiner* — Nicole Kinsey White
(74) *Attorney, Agent, or Firm* — Myers Bigel, P.A.

(57) ABSTRACT

The present invention provides methods and compositions comprising an adeno-associated virus (AAV) capsid protein, comprising one or more amino acids substitutions, wherein the substitutions introduce a new glycan binding site into the AAV capsid protein.

21 Claims, 11 Drawing Sheets

Specification includes a Sequence Listing.

(56) References Cited

OTHER PUBLICATIONS

Figure 1:
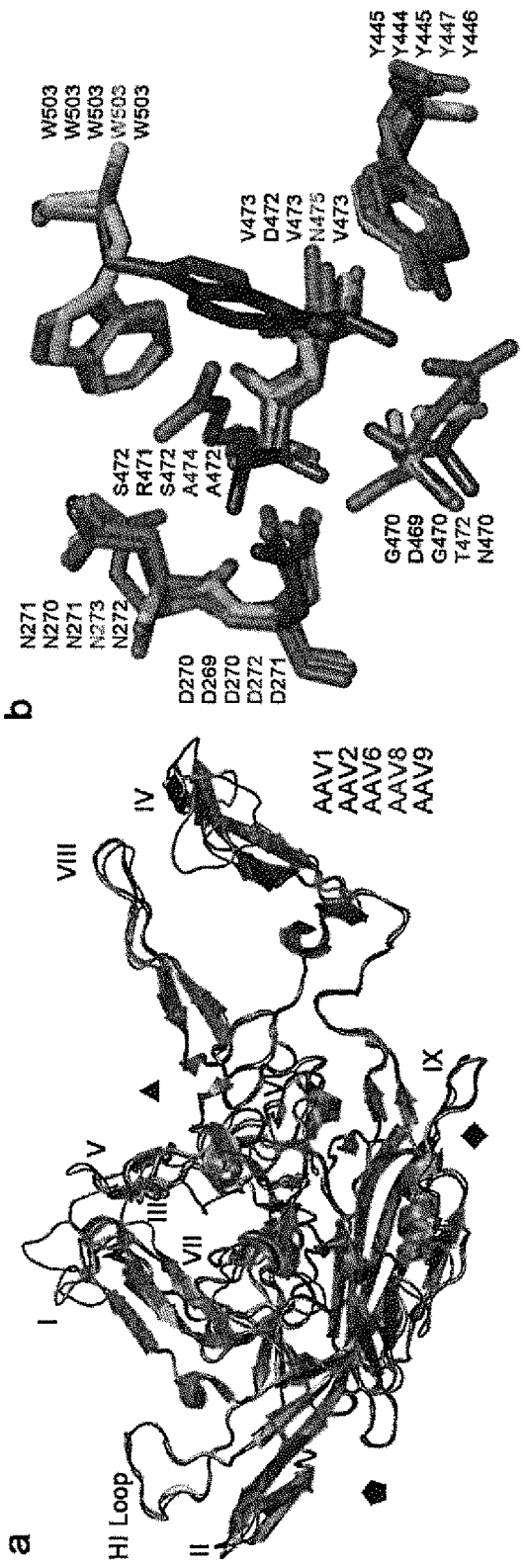

Bell et al. "Identification of the Galactose Binding Domain of the Adeno-Associated Virus Serotype 9 Capsid" *Journal of Virology* 86(13):7326-7333 (2012).
Brichard et al. "The Tyrosinase Gene Codes for an Antigen Recognized by Autologous Cytolytic T Lymphocytes on Hla-A2 Melanomas" *The Journal of Experimental Medicine* 178:489-495 (1993).
Carrillo-Tripp et al. "VIPERdb$^2$: an enhanced and web API enabled relational database for structural virology" *Nucleic Acids Research* 37:D436-D442 (2009).
Chao et al. "Several Log Increase in Therapeutic Transgene Delivery by Distinct Adeno-Associated Viral Serotype Vectors" *Molecular Therapy* 2(6):619-623 (2000).
Chiorini et al. "Cloning of Adeno-Associated Virus Type 4 (AAV4) and Generation of Recombinant AAV4 Particles" *Journal of Virology* 71(9):6823-6833 (1997).
Chiorini et al. "Cloning and Characterization of Adeno-Associated Virus Type 5" *Journal of Virology* 73(2)1309-1319 (1999).
Conway et al. "High-titer recombinant adeno-associated virus production utilizing a recombinant herpes simplex virus type I vector expressing AAV-2 Rep and Cap" *Gene Therapy* 6:986-993 (1999).
Dimattia et al. "Structural Insight into the Unique Properties of Adeno-Associated Virus Serotype 9" *Journal of Virology* 86(12):6947-6958 (2012).
Fang et al. "Stable antibody expression at therapeutic levels using the 2A peptide" *Nature Biotechnology* 23(5):584-590 (2005).
Ferrari et al. "New developments in the generation of Ad-free, high-titer rAAV gene therapy vectors" *Nature Medicine* 3(11):1295-1297 (1997).
Gao et al. "Novel adeno-associated viruses from rhesus monkeys as vectors for human gene therapy" *Proceedings of the National Academy of Sciences* 99(18):11854-11859 (2002).
Gao et al. "Clades of Adeno-Associated Viruses Are Widely Disseminated in Human Tissues" *Journal of Virology* 78(12):6381-6388 (2004).
GenBank Accession No. AAS99264 "Capsid protein VP1 [Adeno-associated virus 9]" *NCBI* (2 pages) (Jun. 24, 2004).
GenBank Accession No. AF513851 "Adeno-associated virus 7 nonstructural protein and capsid protein genes, complete cds" *NCBI* (3 pages) (Sep. 5, 2002).
GenBank Accession No. AF513852 "Adeno-associated virus 8 nonstructural protein and capsid protein genes, complete cds" *NCBI* (3 pages) (Sep. 5, 2002).
GenBank Accession No. J00306 "Human somatostatin I gene and flanks" *NCBI* (2 pages) (Jan. 13, 1995).
Gorman et al. "Stable alteration of pre-mRNA splicing patterns by modified U7 small nuclear RNAs" *Proceedings of the National Academy of Sciences USA* 95:4929-4934 (1998).
Gregorevic et al. "Systemic Microdystrophin Gene Delivery Improves Skeletal Muscle Structure and Function in Old Dystrophic mdx Mice" *Molecular Therapy* 16(4):657-664 (2008).
Grieger et al. "Production and characterization of adeno-associated viral vectors" *Nature Protocols* 1(3):1412-1428 (2006).
Halbert et al. "Adeno-Associated Virus Type 6 (AAV6) Vectors Mediate Efficient Transduction of Airway Epithelial Cells in Mouse Lungs Compared to That of AAV2 Vectors" *Journal of Virology* 75(14):6615-6624 (2001).
Herfst et al. "Airborne Transmission of Influenza A/H5N1 Virus Between Ferrets" *Science* 336:1534-1541 (2012).
High, Katherine A. "The gene therapy journey for hemophilia: are we there yet?" *Blood* 120(23):4482-4487 (2012).
Hoshijima et al. "Chronic suppression of heart-failure progression by a pseudophosphorylated mutant of phospholamban via in vivo cardiac rAAV gene delivery" *Nature Medicine* 8(8):864-871 (2002).
Imai et al. "Experimental adaptation of an influenza H5 HA confers respiratory droplet transmission to a reassortant H5 HA/H1N1 virus in ferrets" *Nature* 486:420-430 (2012).

Inagaki et al. "Robust Systemic Transduction with AAV9 Vectors in Mice: Efficient Global Cardiac Gene Transfer Superior to That of AAV8" *Molecular Therapy* 14(1):45-53 (2006).
Kawakami et al. "Cloning of the gene coding for a shared human melanoma antigen recognized by autologous T cells infiltrating into tumor" *Proceedings of the National Academy of Sciences USA* 91:3515-3519 (1994).
Kawakami et al. "Identification of the Immunodominant Peptides of the MART-1 Human Melanoma Antigen Recognized by the Majority of HLA-A2-restricted Tumor Infiltrating Lymphocytes" *The Journal of Experimental Medicine* 180:347-352 (1994).
Kern et al. "Identification of a Heparin-Binding Motif on Adeno-Associated Virus Type 2 Capsids" *Journal of Virology* 77(20):11072-11081 (2003).
Lerch et al. "Identification of the heparin binding site on adeno-associated virus serotype 3B (AAV-3B)" *Virology* 423(1):6-13 (2012).
Levine, Arnold J. "The Tumor Suppressor Genes" *Annual Review of Biochemistry* 62:623-651 (1993).
Levy et al. "Heparin binding induces conformational changes in Adeno-associated virus serotype 2" *Journal of Structural Biology* 165(3):146-156 (2009).
Li et al. "Construction of phospholamban antisense RNA recombinant adeno-associated virus vector and its effects in rat cardiomyocytes" *Acta Pharmacologica Sinica* 26(1):51-55 (2005).
McCarty, Douglas M. "Self-complementary AAV Vectors; Advances and Applications" *Molecular Therapy* 16(10):1648-1656 (2008).
Mingozzi et al. "Therapeutic in vivo gene transfer for genetic disease using AAV: progress and challenges" *Nature Reviews Genetics* 12:341-355 (2011).
Miyamura et al. "Parvovirus particles as platforms for protein presentation" *Proceedings of the National Academy of Sciences USA* 91:8507-8511 (1994).
Muramatsu et al. "Nucleotide Sequencing and Generation of an Infectious Clone of Adeno-Associated Virus 3" *Virology* 221:208-217 (1996).
NCBI Reference: NC_001401 "Adeno-associated virus—2, complete genome" *NCBI* (7 pages) (Dec. 2, 2014).
NCBI Reference: NC_001729 "Adeno-associated virus—3, complete genome" *NCBI* (3 pages) (Jun. 28, 2010).
NCBI Reference: NC_001829 "Adeno-associated virus—4, complete genome" *NCBI* (3 pages) (Jan. 28, 2010).
NCBI Reference: NC_001862 "Adeno-associated virus 6, complete genome" *NCBI* (3 pages) (Jan. 12, 2004).
NCBI Reference: NC_001863 "Adeno-associated virus 3B, complete genome" *NCBI* (3 pages) (Jan. 12, 2004).
NCBI Reference: NC_002077 "Adeno-associated virus—1, complete genome" *NCBI* (3 pages) (Mar. 11, 2010).
NCBI Reference: NC_006152 "Adeno-associated virus 5, complete genome" *NCBI* (3 pages) (Dec. 8, 2008).
NCBI Reference: YP_680426 "Major coat protein VP1 [Adeno-associated virus—2]" *NCBI* (2 pages) (Nov. 19, 2010).
Neu et al. "Viruses and Sialic Acids: Rules of Engagement" *Current Opinion in Structural Biology* 21(5):610-618 (2011).
Ng et al. "Structural Characterization of the Dual Glycan Binding Adeno-Associated Virus Serotype 6" *Journal of Virology* 84(24):12945-12957 (2010).
O'Donnell et al. "Adeno-Associated Virus-2 and its Primary Cellular Receptor—Cryo-EM Structure of a Heparin Complex" *Virology* 385(2):434-443 (2009).
Opie et al. "Identification of Amino Acid Residues in the Capsid Proteins of Adeno-Associated Virus Type 2 That Contribute to Heparan Sulfate Proteoglycan Binding" *Journal of Virology* 77(12):6995-7006 (2003).
Padron et al. "Structure of Adeno-Associated Virus Type 4" *Journal of Virology* 79(8):5047-5058 (2005).
Palombo et al. "Site-Specific Integration in Mammalian Cells Mediated by a New Hybrid Baculovirus-Adeno-Associated Virus Vector" *Journal of Virology* 72(6):5025-5034 (1998).
Puttaraju et al. "Spliceosome-mediated RNA trans-splicing as a tool for gene therapy" *Nature Biotechnology* 17:246-252 (1999).
Robbins et al. "Recognition of Tyrosinase by Tumor-infiltrating Lymphocytes from a Patient Responding to Immunotherapy" *Cancer Research* 54:3124-3126 (1994).

(56) References Cited

OTHER PUBLICATIONS

Rosenberg, Steven A. "The Immunotherapy of Solid Cancers Based on Cloning the Genes Encoding Tumor-Rejection Antigens" *Annual Review of Medicine* 47:481-491 (1996).

Rosenberg, Steven A. "A New Era for Cancer Immunotherapy Based on the Genes that Encode Cancer Antigens" *Immunity* 10:281-287 (1999).

Shade et al. "Nucleotide Sequence and Genome Organization of Human Parvovirus B19 Isolated from the Serum of a Child during Aplastic Crisis" *Journal of Virology* 58(3):921-936 (1986).

Shen et al. "Terminal N-Linked Galactose Is the Primary Receptor for Adeno-associated Virus 9" *The Journal of Biological Chemistry* 286(15):13532-13540 (2011).

Srivastava et al. "Nucleotide Sequence and Organization of the Adeno-Associated Virus 2 Genome" *Journal of Virology* 45(2):555-564 (1983).

Summerford et al. "Membrane-Associated Heparan Sulfate Proteoglycan Is a Receptor for Adeno-Associated Virus Type 2 Virions" *Journal of Virology* 72(2):1438-1445 (1998).

Tinsley et al. "Amelioration of the dystrophic phenotype of *mdx* mice using a truncated utrophin transgene" *Nature* 384:349-353 (1996).

Tsao et al. "The Three-Dimensional Structure of Canine Parvovirus and Its Functional Implications" *Science* 251(5000):1456-1464 (1991).

UniProtKB/Swiss-Prot: P01166 "Somatostatin precursor [Contains: Somatostatin-28; Somatostatin-14]" *NCBI* (3 pages) (Sep. 15, 2003).

Urabe et al. "Insect Cells as a Factory to Produce Adeno-Associated Virus Type 2 Vectors" *Human Gene Therapy* 13:1935-1943 (2002).

Vincent et al. "Long-term correction of mouse dystrophic degeneration by adenovirus-mediated transfer of a minidystrophin gene" *Nature Genetics* 5:130-134 (1993).

Walters et al. "Structure of Adeno-Associated Virus Serotype 5" *Journal of Virology* 78(7):3361-3371 (2004).

Wang et al. "Adeno-associated virus vector carrying human minidystrophin genes effectively ameliorates muscular dystrophy in *mdx* mouse model" *Proceedings of the National Academy of Sciences* 97(25):13714-13719 (2000).

Wang et al. "Existence of transient functional double-stranded DNA intermediates during recombinant AAV transduction" *Proceedings of the National Academy of Sciences* 104(32):13104-13109 (2007).

Wang et al. "AAV8-mediated Hepatic Gene Transfer in Infant Rhesus Monkeys (*Macaca mulatta*)" *Molecular Therapy* 19(11):2012-2020 (2011).

Wu et al. "Single Amino Acid Changes Can Influence Titer, Heparin Binding, and Tissue Tropism in Different Adeno-Associated Virus Serotypes" *Journal of Virology* 80(22):11393-11397 (2006).

Xiao et al. "Gene Therapy Vectors Based on Adeno-Associated Virus Type 1" *Journal of Virology* 73(5):3994-4003 (1999).

Xie et al. "The atomic structure of adeno-associated virus (AAV-2), a vector for human gene therapy" *Proceedings of the National Academy of Sciences* 99(16):10405-10410 (2002).

Xie et al. "Structure-function Analysis of Receptor-binding in Adeno-Associated Virus Serotype 6 (AAV-6)" *Virology* 420(1):10-19 (2011).

Zhang et al. "Recombinant adenovirus expressing adeno-associated virus cap and rep proteins supports production of high-titer recombinant adeno-associated virus" *Gene Therapy* 8:704-712 (2001).

Zhong et al. "Next generation of adeno-associated virus 2 vectors: Point mutations in tyrosines lead to high-efficiency transduction at lower doses" *Proceedings of the National Academy of Sciences* 105(22):7827-7832 (2008).

Zincarelli et al. "Analysis of AAV Serotypes 1-9 Mediated Gene Expression and Tropism in Mice After Systemic Injection" *Molecular Therapy* 16(6):1073-1080 (2008).

Zolotukhin et al. "Recombinant adeno-associated virus purification using novel methods improves infectious titer and yield" *Gene Therapy* 6:973-985 (1999).

Dickey et al. "Enhanced Sialic Acid-Dependent Endocytosis Explains the Increased Efficiency of Infection of Airway Epithelia by a Novel Adeno-Associated Virus" *Journal of Virology* 85(17):9023-9030 (2011).

International Search Report and the Written Opinion of the International Searching Authority corresponding to International Patent Application No. PCT/US2014/028545 (7 pages) (dated Jul. 16, 2014).

Murray et al. "Characterization of the Capsid Protein Glycosylation of Adeno-Associated Virus Type 2 by High-Resolution Mass Spectrometry" *Journal of Virology* 80(12):6171-6176 (2006).

International Preliminary Report on Patentability corresponding to International Patent Application No. PCT/US2014/028545 (6 pages) (dated Sep. 15, 2015).

Adachi et al. "Creation of a Novel AAV2 Vector Showing AAV9-Like Transduction Properties by Displaying a Galactose Binding Motif on the Capsid" *American Society of Gene & Cell Therapy* Final Program Addendum, 15th Annual Meeting, 816:34-35 (2012).

Adachi et al. "Drawing a high-resolution functional map of adeno-associated virus capsid by massively parallel sequencing" *Nature Communications* 5(3075):1-14 (2014).

Asokan et al. "An Emerging Adeno-Associated Viral Vector Pipeline for Cardiac Gene Therapy" *Human Gene Therapy* 24:906-913 (2013).

Extended European Search Report corresponding to European Patent Application No. 14763050.3 (12 pages) (dated Nov. 25, 2016).

Klimczak et al. "A Novel Adeno-Associated Viral Variant for Efficient and Selective Intravitreal Transduction of Rat Müller Cells" *PLoS One* 4(10):e7467 (2009).

Koerber et al. "DNA Shuffling of Adeno-associated Virus Yields Functionally Diverse Viral Progeny" *Molecular Therapy* 16(10):1703-1709 (2008).

Shen et al. "Engraftment of a Galactose Receptor Footprint onto Adeno-associated Viral Capsids Improves Transduction Efficiency" *The Journal of Biological Chemistry* 288(40):28814-28823 (2013).

METHODS AND COMPOSITIONS FOR DUAL GLYCAN BINDING AAV VECTORS

STATEMENT OF PRIORITY

This application is a 35 U.S.C. § 371 national phase application of International Application Serial No. PCT/US2014/028545, filed Mar. 14, 2014, which claims the benefit, under 35 U.S.C. § 119(e), of U.S. Provisional Application Ser. No. 61/802,111, filed Mar. 15, 2013, the entire contents of which are incorporated by reference herein.

STATEMENT OF GOVERNMENT SUPPORT

This invention was made with government support under Grant Numbers HL089221, AI072176 and HL112761 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-664TS_ST25.txt, 28,767_bytes in size, generated on Apr. 19, 2018 and filed via EFS-Web, is provided in lieu of a paper copy. This Sequence Listing is hereby incorporated by reference into the specification for its disclosures.

FIELD OF THE INVENTION

The present invention relates to modified capsid proteins from adeno-associated virus (AAV), virus capsids and virus vectors comprising the same, as well as methods of their use.

BACKGROUND OF THE INVENTION

Virus-glycan interactions are critical determinants of host cell invasion. Cell surface carbohydrates such as sialic acids, gangliosides or heparan sulfate are exploited by a vast number of viruses such as influenza, herpesvirus, SV40, polyomavirus, papillomavirus and other pathogens[1,2]. In most cases, a single class of glycans primarily serves as the cell surface attachment factor for viruses, leading to sequential or parallel engagement of other receptors/co-receptors for cell entry. Adeno-associated viruses (AAV) are helper-dependent parvoviruses that exploit heparan sulfate (HS), galactose (Gal) or sialic acids (Sia) as primary receptors for cell surface binding[3,4]. For instance, AAV serotypes 2 and 3b utilize HS; AAV1, 4 and 5 bind Sia with different linkage specificities; while AAV9 exploits Gal for host cell attachment. Different AAV strains also require subsequent interaction with co-receptors such as integrin $\alpha V \beta 5$ or $\alpha 5 \beta 1$, fibroblast growth factor receptor (FGFR), platelet-derived growth factor receptor (PDGFR), epidermal growth factor receptor (EGFR), hepatocyte growth factor receptor (HGFR) or the laminin receptor for cellular uptake[3,4].

A notable exception to the monogamous relationship between a specific AAV strain and a single class of carbohydrates is AAV serotype 6, which recognizes both Sia and HS[5]. However, only Sia has been shown essential for viral transduction. Structural studies have now established that the K531 residue in conjunction with R488, K528 and K533 in the VP3 subunit of the AAV6 capsid form a continuous basic patch for electrostatic recognition of HS glycosaminoglycans[6-8]. Similarly, the structural basis for HS recognition by AAV2 and AAV3b is well known and attributed to similar clusters of basic amino acid residues located at the three-fold axis of symmetry[9-12]. The Sia binding footprints for AAV1, AAV4, AAV5 and AAV6 remain to be determined. More recently, key amino acid residues involved in Gal recognition by AAV9 capsids were identified by using a combination of molecular docking and site-directed mutagenesis[13]. What is needed are virus vectors that have multiple glycan binding capability to exploit alternative pathways for cell entry and transduction.

The present invention overcomes previous shortcomings in the art by providing modified capsid proteins with multiple glycan binding sites, AAV vectors comprising these capsid proteins and methods for their use as therapeutic vectors.

SUMMARY OF THE INVENTION

In one aspect, the present invention provides an adeno-associated virus (AAV) capsid protein, comprising one or more amino acids substitutions, wherein the substitutions introduce a new glycan binding site into the AAV capsid protein. In some embodiments, the amino acid substitutions are in amino acid 266, amino acids 463-475 and amino acids 499-502 in AAV2 or the corresponding amino acid positions in AAV1, AAV3, AAV4, AAV5, AAV6, AAV7, AAV8 or AAV10.

In some embodiments, new glycan binding site can be a hexose binding site, wherein the hexose is a galactose (Gal), a mannose (Man), a glucose (Glu) or a fucose (fuc).

In some embodiments, the new glycan binding site can be a sialic acid (Sia) binding site, wherein the Sia residue is N-acetylneuraminic acid (Neu5Ac) or N-Glycolylneuraminic acid (Neu5Gc).

In some embodiments, the new glycan binding site can be a disaccharide binding site, wherein the disaccharide is a sialic acid linked to galactose in the form Sia(alpha2,3)Gal or Sia(alpha2,6)Gal.

In some embodiments, the substitutions introduce a new glycan binding site from a first AAV serotype into the capsid protein of a second AAV serotype that is different from said first AAV serotype.

The present invention also provides an AAV capsid comprising the AAV capsid protein of this invention.

Further provided herein is a virus vector comprising the AAV capsid of this invention as well as a composition comprising the AAV capsid protein, AAV capsid and/or virus vector of this invention in a pharmaceutically acceptable carrier.

The present invention additionally provides a method of introducing a nucleic acid into a cell, comprising contacting the cell with the virus vector of this invention. The cell can be in a subject and in some embodiments, the subject can be a human subject.

These and other aspects of the invention are addressed in more detail in the description of the invention set forth below.

BRIEF DESCRIPTION OF THE DRAWINGS

FIG. 1. Structural alignment of AAV1, AAV2, AAV6, AAV8, and AAV9 VP3 monomers. (Panel A) Superposition of the VP3 monomers of AAV1 (purple blue), AAV2 (deep blue), AAV6 (light magenta), AAV8 (green), and AAV9 (brown) with loops I-IX labeled and axes of symmetry indicated. (Panel B) Close-up views of overlay of the galactose binding site on AAV9 and equivalent residues on AAV1, AAV2, AAV6, and AAV8 Amino acid residues are marked by the color code in (Panel A). Coordinates were obtained from X-ray crystallography structure of VP monomers (PDB accession#: AAV1-3NG9, AAV2-1LP3, AAV6-3OAH, AAV8-2QA0, AAV9-3UX1). Structure alignment was performed and visualized using PyMOL.

Figure 2:
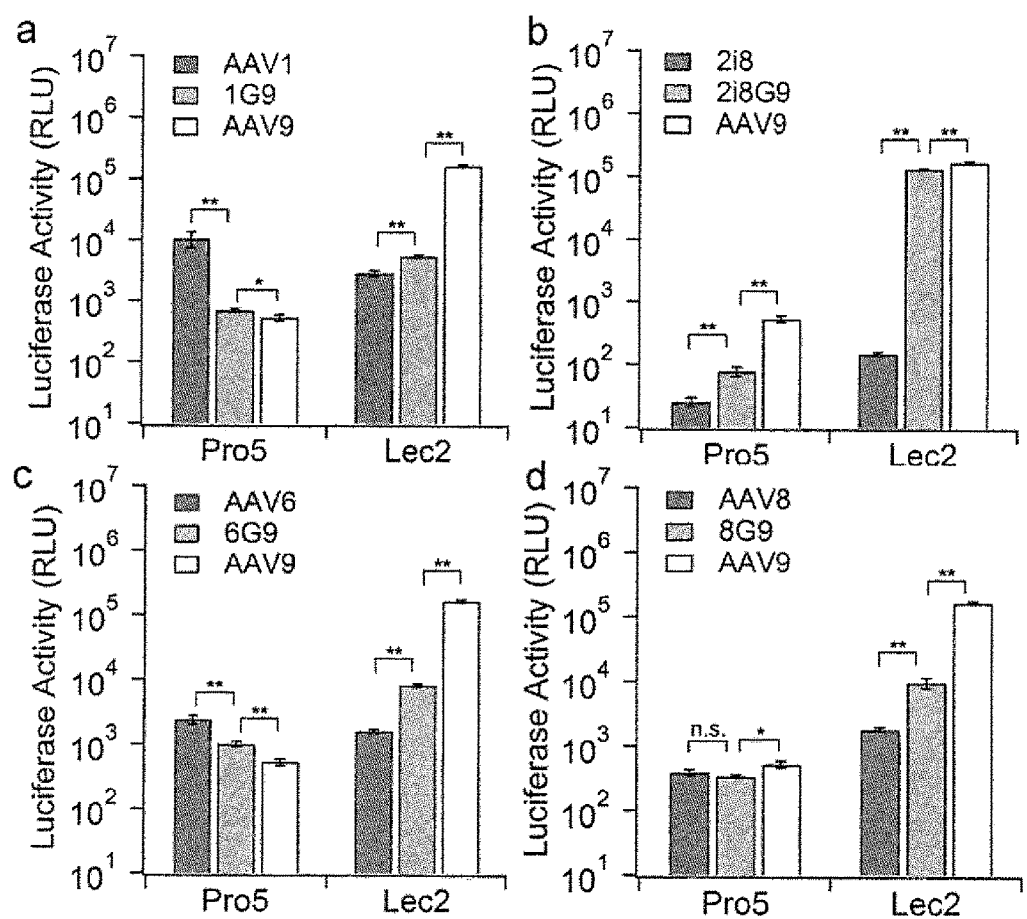

FIG. 2. G-mutants utilize Gal as a novel glycan receptor to transduce cells in vitro. (Panel A) Transduction efficiency of AAV1, 1G9, and AAV9 on Chinese Hamster Ovary (CHO) cell lines. Pro5 and Lec2 cells were pre-chilled to 4° C. for 30 minutes prior to AAV-CBA-Luciferase infection at an MOI of 1000 vg/cell at 4° C. for 60 minutes. After removing unbound virions by three washes with ice-cold PBS, infected cells were cultured in 37° C. incubator for 24 hours. Luminometric analysis was performed to quantify the luciferase transgene expression efficiencies from cell lysates. (Panel B) Transduction efficiency of AAV2i8, 2i8G9, and AAV9 on Pro5 and Lec2 cells. (Panel C) Transduction efficiency of AAV6, 6G9, and AAV9 on Pro5 and Lec2 cells. (Panel D) Transduction efficiency of AAV8, 8G9, and AAV9 on Pro5 and Lec2 cells. Results are presented as mean±s.e.m. (n=4). Statistical significance was assessed using the one-tailed Student's t-test (n.s., not significant; *$p<0.05$; **$p<0.01$).

Figure 3:
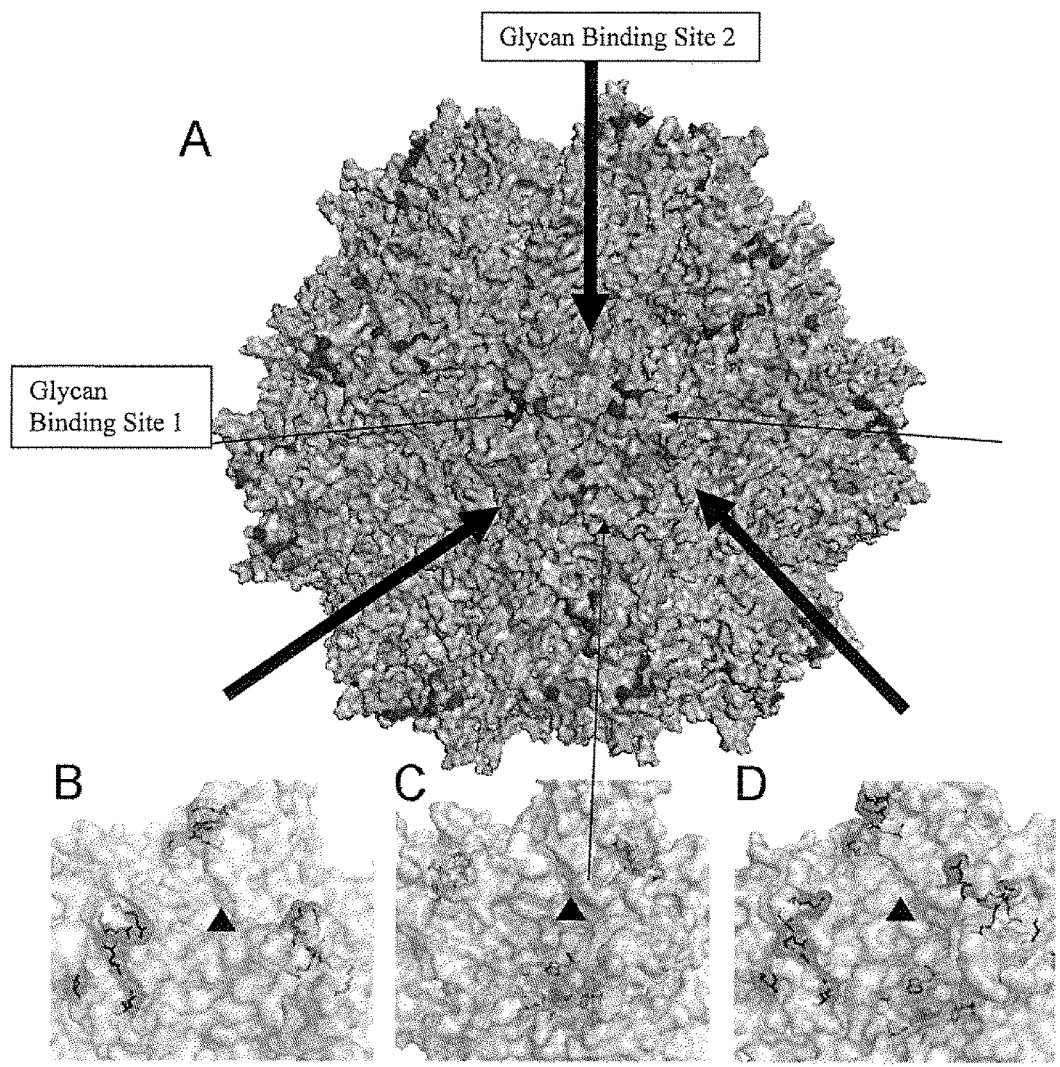

FIG. 3. Three-dimensional models of the dual glycan binding AAV2G9 chimera and its parental strains AAV2 and AAV9. (Panel A) Three-dimensional structural model of an intact AAV2G9 capsid with existing HS and "grafted" Gal binding sites colored in purple and orange, respectively. (Panels B-D) Illustrations of the three-dimensional surface model of VP3 trimers at the three-fold symmetry axes of AAV2 (Panel B), AAV9 (Panel C), and AAV2G9 (Panel D) capsids. Residues involved in HS binding (AAV2 VP1 numbering: R487, K527, K532, R585, R588) and Gal binding (AAV9 VP1 numbering: D271, N272, Y446, N470, A472, V473, W503) are highlighted as in (Panel A). Black triangles indicate the three-fold symmetry axes.

Figure 4:
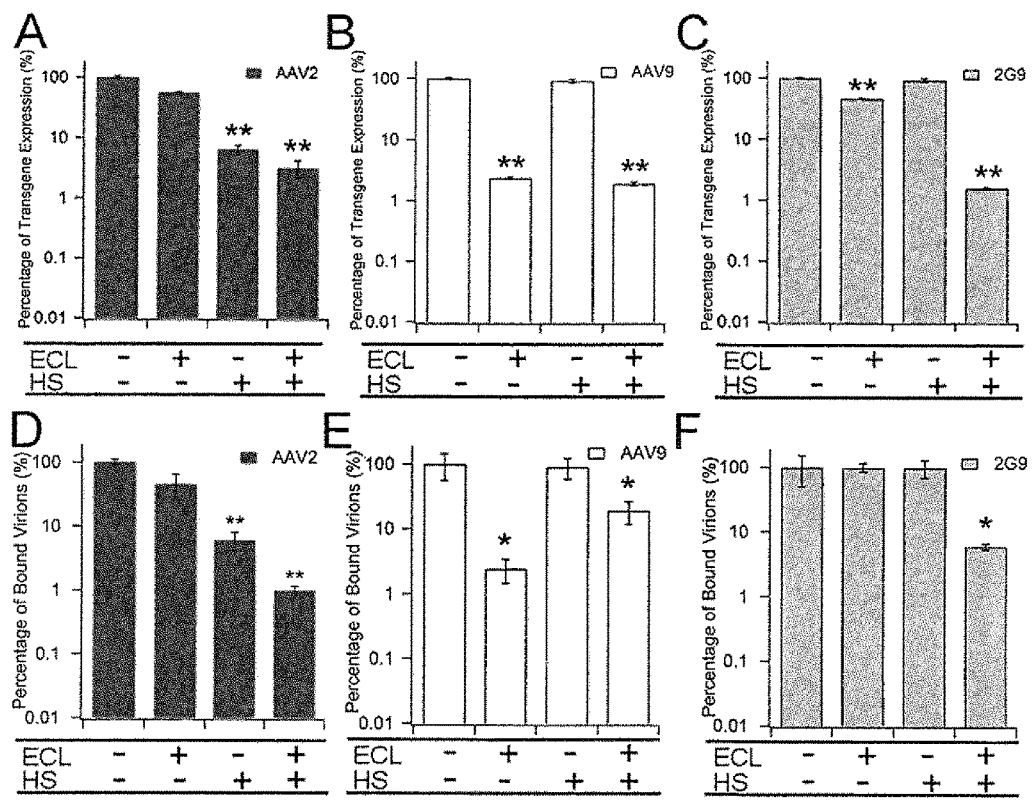

FIG. 4. In vitro characterization of the dual glycan binding AAV2G9 chimera. (Panels A-C) Inhibition of AAV2 (Panel A), AAV9 (Panel B), and AAV2G9 (Panel C) transduction on CHO Lec2 cells with FITC-ECL and soluble heparin. CHO Lec2 cells were pre-chilled at 4° C. and incubated with FITC-ECL, soluble heparin or both prior to infection with AAV2, AAV9 or AAV2G9 packaging a CBA-luciferase reporter transgene cassette. Transduction efficiency was measured 24 hours post infection as luciferase activity in relative light units (RLU). Percentage of transgene expression was calculated by normalizing transduction efficiency to RLU from controls. Results are presented as mean±s.e.m. (n=4). (Panels D-F) Competitive inhibition of cell surface binding of AAV2 (Panel D), AAV9 (Panel E), and AAV2G9 (Panel F) on CHO Lec2 cells with FITC-ECL and soluble heparin. Different AAV particles were bound to cells pre-chilled at 4° C. and unbound virions removed by washing with cold PBS. Bound virions were quantified using qPCR after viral genome extraction. Percentage of bound virions was determined by normalizing number of bound virions to that of corresponding controls. Results are presented as mean s.e.m. (n=5). Statistical significance was analyzed using the one-tailed Student's t-test (*$p<0.05$; **$p<0.01$).

Figure 5:
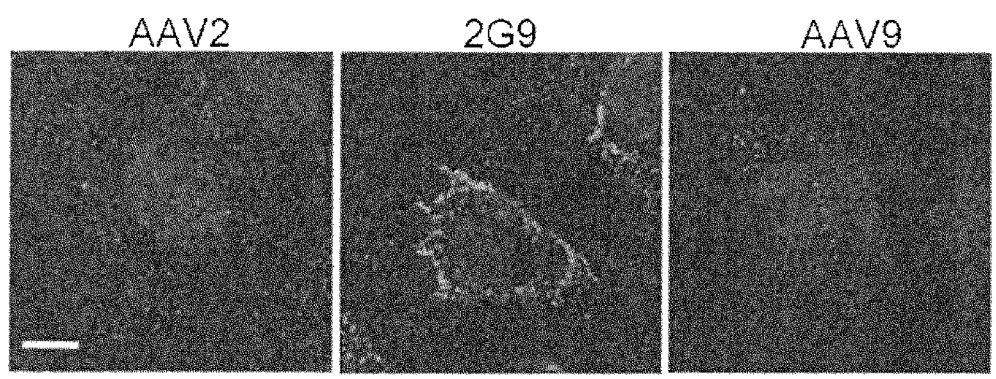

FIG. 5. Immunofluorescence of bound virions on Lec2 cell surface at 0 hours post-infection (hpi). CHO Lec2 cells were plated on 12 mm coverslips at density of $5\times10^4$ cells/coverslip overnight. After being pre-chilled at 4° C. for 30 minutes, Lec2 cells were infected with AAV2, AAV 2G9, and AAV9 at an MOI of 1000 vg/cell at 4° C. for 30 minutes. After removal of unbound virions, cells were fixed with 2% paraformaldehyde in 1×PBS. Intact virions were detected using the monoclonal antibodies (A20 for AAV2/AAV2G9 and ADK9 for AAV9) obtained as media supernatant from corresponding hybridoma cultures with 1:10 dilution in immunofluorescence wash buffer (IFWB). ALEXA FLUOR 594® goat anti-mouse IgG was utilized at a dilution of 1:1000 in IFWB as the secondary antibody for immunofluorescence detection. Coverslips were then mounted onto glass slides in PROLONG® Gold anti-fade reagent with DAPI. Fluorescence micrographs were acquired using a ZEISS® 710 confocal laser scanning microscope equipped with a 63× oil immersion objective and a spectral detection system. Image processing was carried out using LSM® viewer and IMAGE J® software. The white scale bar indicates 10 µm.

Figure 6:
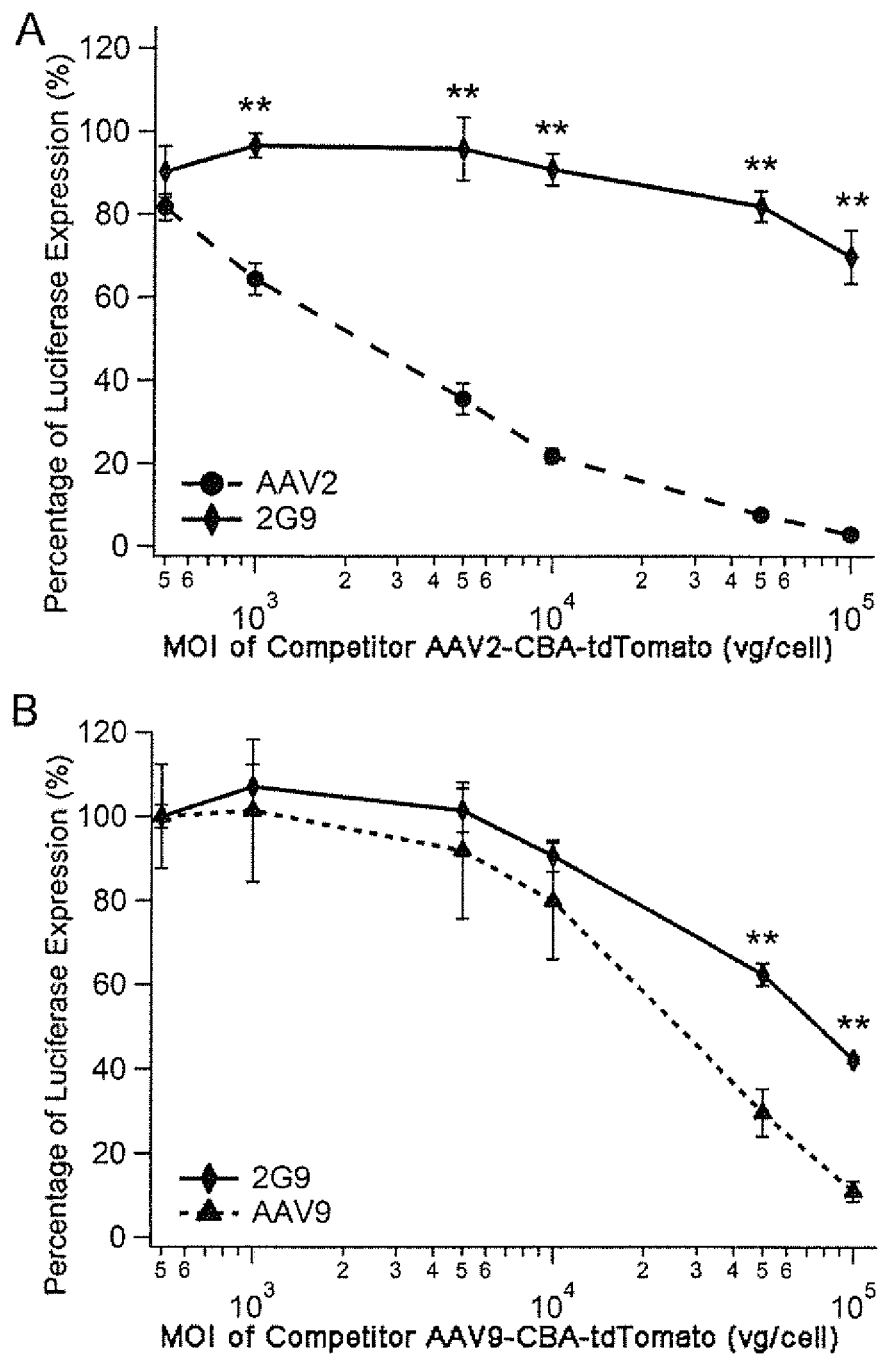

FIG. 6. Competitive inhibition of AAV2G9 transduction on Lec2 cells by AAV2 capsids or AAV9 capsids. Lec2 cells were preincubated with (Panel A) AAV2 or (Panel B) AAV9-CBA-tdTomato at multiplicity of infection (MOI) ranging from 500 to 100,000 vg/cell for 2 hours prior to infection with AAV2G9-CBA-Luc particles (MOI 1000 vg/cell). Percentage inhibition of AAV2G9 transduction was calculated by normalizing luciferase transgene expression levels to that of untreated control. Results are presented as mean±s.e.m. (n=4). Statistical significance was analyzed using the one-tailed Student's t-test (*$p<0.05$; **$p<0.01$).

Figure 7:
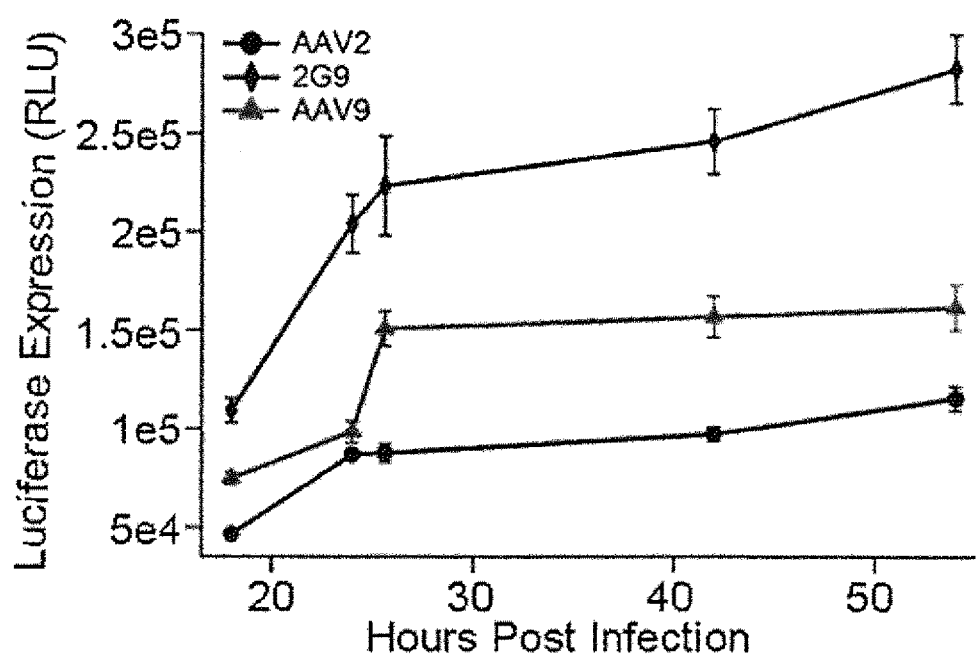

FIG. 7. Kinetics of transduction efficiency profiles of AAV 2G9 compared to parental AAV2 and AAV9 on Lec2 cells at indicated time points post infection. Pre-chilled Lec2 cells were infected with AAV2, AAV2G9, or AAV9-CBA-luciferase vectors at an MOI of 1000 vg/cell as described. At indicated time points (18, 24, 28, 42 and 54 hours) post-infection, cells were lysed prior to luminometric analysis. Luciferase transgene expression was measured by luciferase activities of cell lysates in relative light units (RLU) (n=5). Statistical significance was assessed using the one-tailed Student's t-test (*$p<0.05$; **$p<0.01$).

Figure 8:
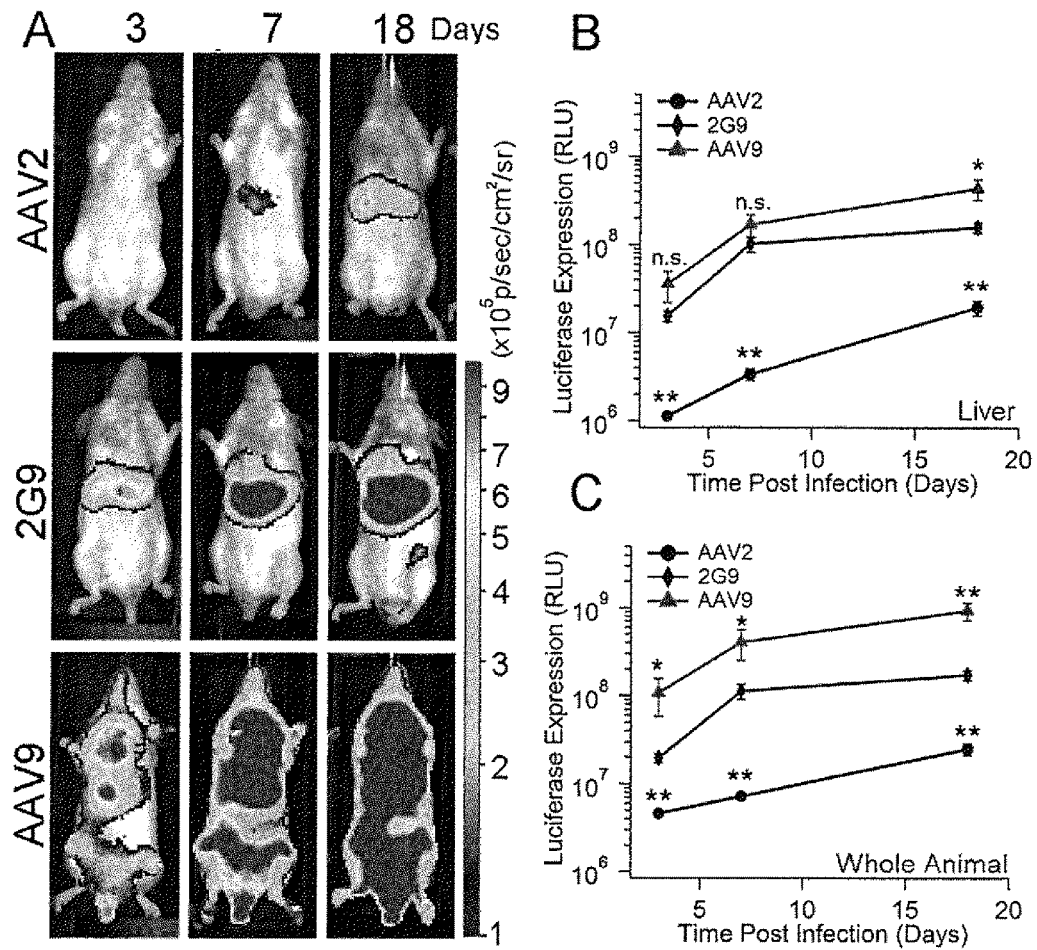

FIG. 8. AAV2G9 mediates rapid onset and enhanced transgene expression in vivo. (Panel A) In vivo transgene expression kinetics of AAV2, AAV 2G9, and AAV9 vectors packaging CBA-luciferase transgene cassette. BALB/c mice (n=4) were administered AAV vectors at a dose of $1\times10^{11}$ vg/animal through the tail vein and bioluminescent images collected at 3, 7, and 18 days post-injection using an XENOGEN® Lumina imaging system. Representative live animal images are shown with bioluminescence on a rainbow colored scale ($1\times10^5$-$1\times10^6$ photons/second/cm$^2$/steradian). AAV2G9 maintains the hepatic tropism of AAV2, but demonstrates a more rapid and robust luciferase signal than both parental AAV strains. (Panel B and C) Quantitation of the kinetics of light signal output (expressed as photons/second/cm$^2$/steradian) was performed by marking regions of interest (ROIs) around images of the (Panel B) liver region and (Panel C) entire animals obtained at different time intervals (n=4). Statistical significance was assessed using the one-tailed Student's t-test (n.s., not significant; *$p<0.05$; **$p<0.01$).

Figure 9:
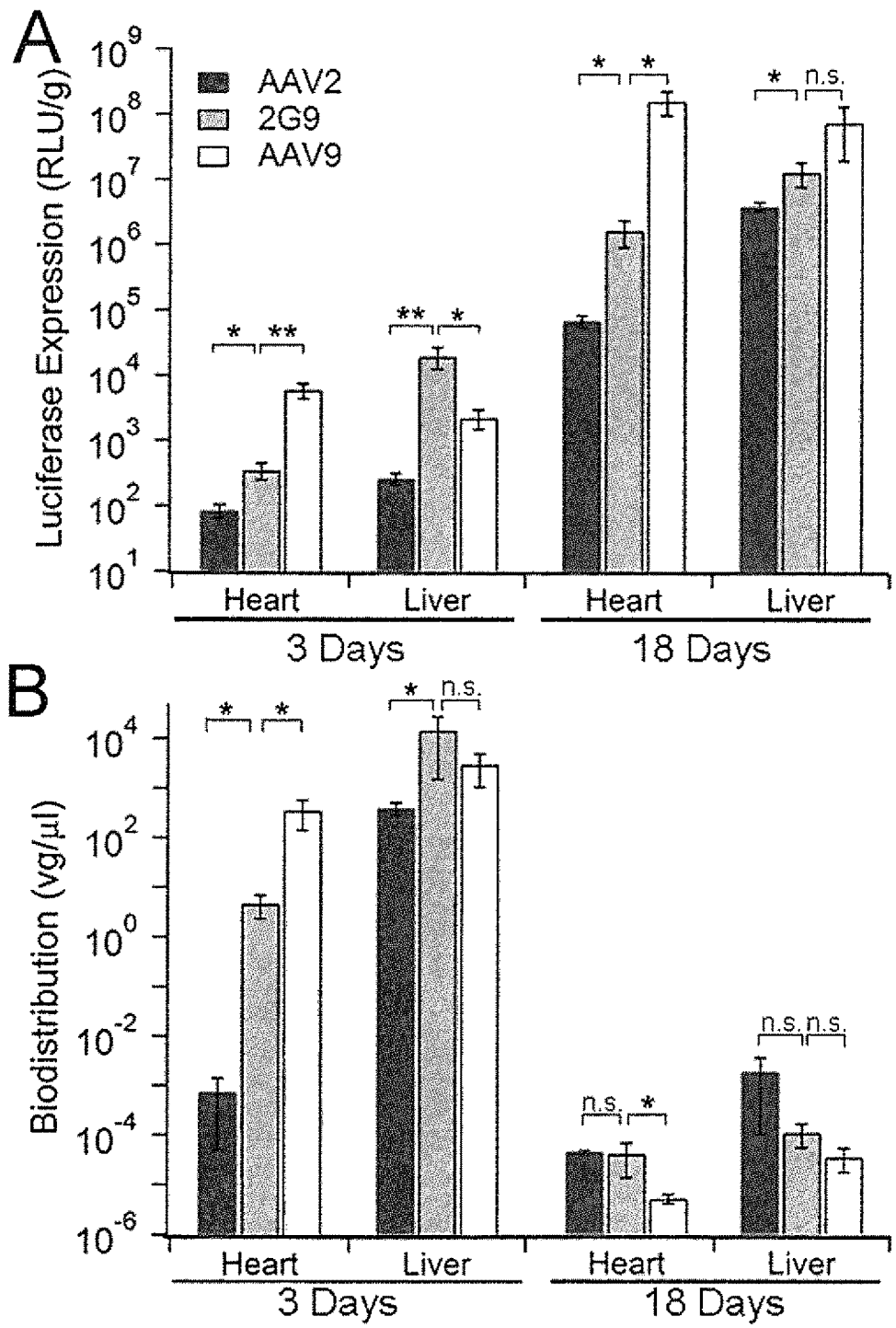

FIG. 9. Quantification of transgene expression and biodistribution profiles of AAV2G9 in mice. (Panel A) Quantitation of luciferase transgene expression from heart and liver tissue lysates of AAV2 (black), AAV2G9 (grey), or AAV9 (white) treated animals at days 3 and 18 (n=4). (Panel B) Biodistribution of vector genomes in liver and heart lysates obtained from BALB/c mice administered with AAV2 (black), AAV2G9 (grey), or AAV9 (white) at days 3 and 18 (n=4). At indicated time points, host genomic DNA and viral genomes were isolated from tissue lysates and quantified using qPCR with primer sets specific to mouse lamin gene and luciferase transgene. Results are presented as mean±s.e.m. (n=4). Statistical significance was assessed using the one-tailed Student's t-test (n.s., not significant; *p<0.05; **p<0.01).

Figure 10:
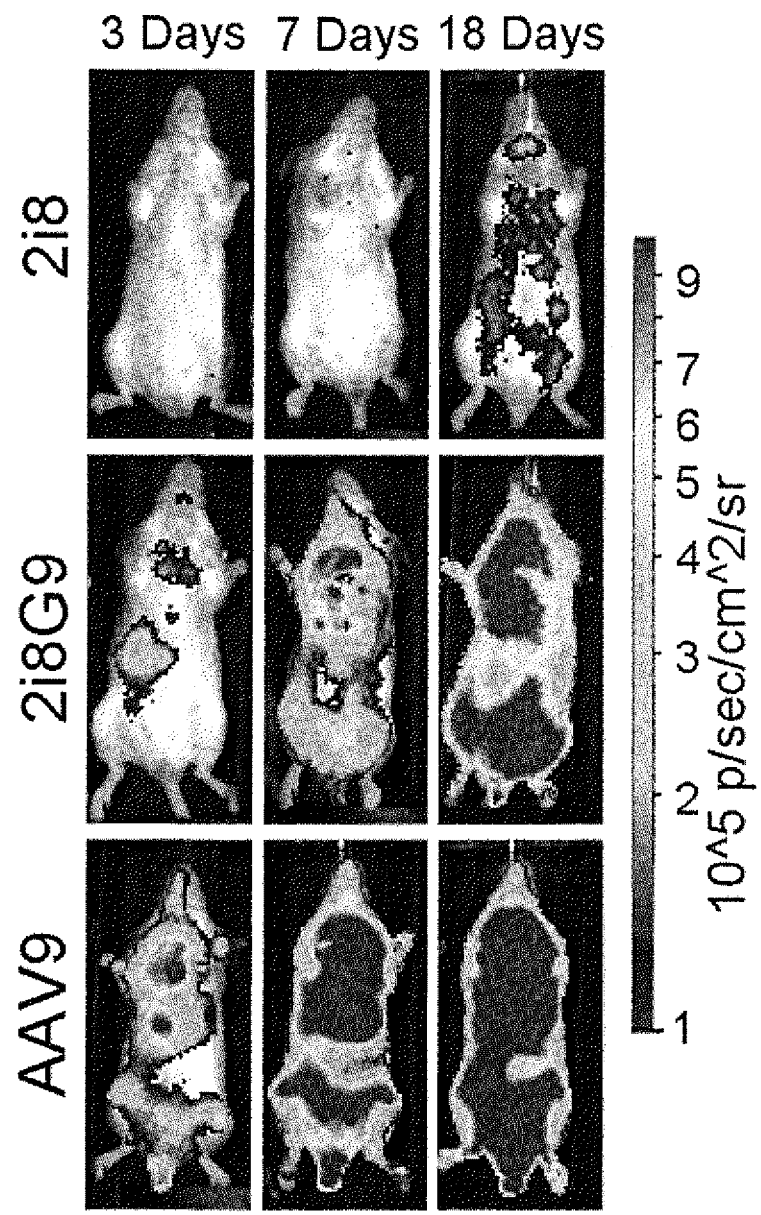

FIG. 10. In vivo transgene expression kinetics of AAV2i8, 2i8G9, and AAV9 vectors packaging CBA-luciferase transgene cassette. BALB/c mice (n=4) were administered AAV vectors at a dose of $1 \times 10^{11}$ vg/animal through the tail vein and bioluminescence images collected at 3, 7, and 18 days post-injection using a XENOGEN® Lumina imaging system. Representative live animal images are shown with bioluminescence expressed on a rainbow colored scale ($10^5$-$10^6$ photons/second/cm$^2$/steradian).

Figure 11:
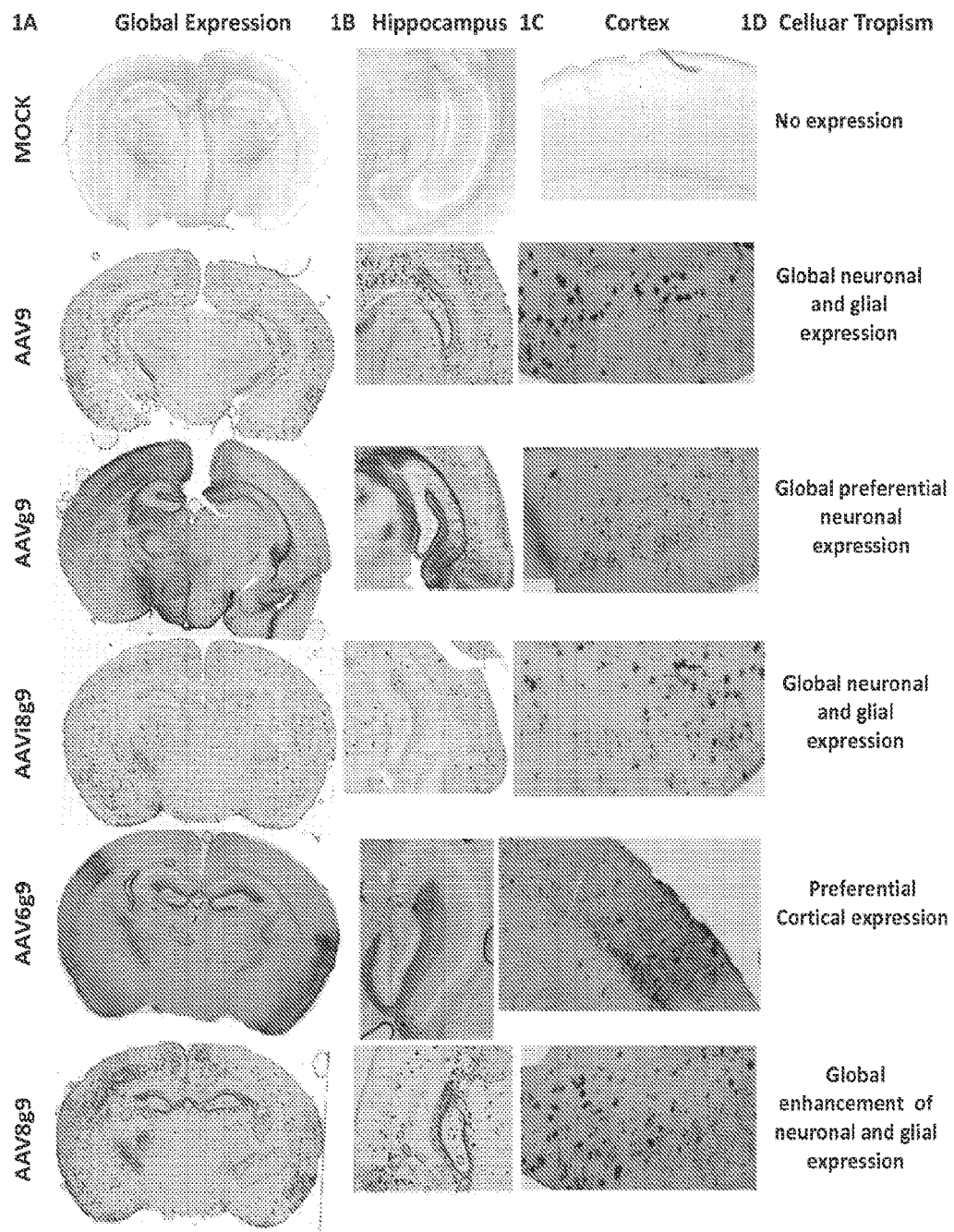

FIG. 11. CNS tropism profiles of representative AAV "G9" strains in neonatal mice. Postnatal 0 (P0) pups (n=3) were unilaterally injected into the left cerebral ventricle with 3.5×10e9 AAV vector genomes containing a GFP transgene driven by a hybrid chicken beta actin (CBh) promoter. At 2 wks post injection, GFP immunohistochemistry revealed differential spread, regional and cellular tropisms for each AAV "G9" strain within the murine brain.

DETAILED DESCRIPTION OF THE INVENTION

The present invention will now be described with reference to the accompanying drawings, in which representative embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference herein in their entirety.

The present invention is based on the discovery of a "pocket" on the AAV capsid protein that defines a glycan recognition footprint. Specific amino acids that define this pocket have been identified and are described herein, for example for the galactose binding site of AAV9. In the present invention, this AAV9 galactose binding footprint was grafted into an AAV2 capsid protein template, resulting in the introduction of a new glycan binding site in the engrafted AAV2 capsid protein template. This AAV galactose binding footprint can be introduced into any other AAV serotype, by substituting the corresponding amino acids, which are shown, for example, in Table 3 herein.

Thus the present invention is directed to molecular grafting of a glycan recognition footprint from one AAV strain onto another, which is guided by structural modeling studies and achieved by site-directed mutagenesis. Recombinant vectors (derived from these new strains) packaging reporter cassettes display rapid onset and enhanced transgene expression in cell culture and animal models. Using naturally occurring serotypes/isolates as templates, this universal strategy can be applied to generate a panel of synthetic dual glycan binding AAV strains that could address challenges such as dose-dependent immunotoxicity observed in human gene therapy clinical trials.

Thus, in one aspect, the present invention provides an adeno-associated virus (AAV) capsid protein, comprising one or more amino acids substitutions, wherein the substitutions introduce a new glycan binding site into the AAV capsid protein. In some embodiments, the amino acid substitutions are in amino acid 266, amino acids 463-475 and amino acids 499-502 in AAV2 or the corresponding amino acid positions in AAV1, AAV3, AAV4, AAV5, AAV6, AAV7, AAV8, AAV10 or any other AAV serotype as identified in Table 3.

In some embodiments, the new glycan binding site can be a hexose binding site, wherein the hexose is a galactose (Gal), a mannose (Man), a glucose (Glu) or a fucose (fuc).

In some embodiments, the new glycan binding site can be a sialic acid (Sia) binding site, wherein the Sia residue is N-acetylneuraminic acid (Neu5Ac) or N-Glycolylneuraminic acid (Neu5Gc).

In some embodiments, the new glycan binding site can be a disaccharide binding site, wherein the disaccharide is a sialic acid linked to galactose in the form Sia(alpha2,3)Gal or Sia(alpha2,6)Gal.

In some embodiments, the substitutions introduce a new glycan binding site from a capsid protein of a first AAV serotype ("donor") into the capsid protein of a second AAV serotype ("template) that is different from said first AAV serotype.

The present invention also provides an AAV capsid comprising the AAV capsid protein of this invention.

Further provided herein is a virus vector comprising the AAV capsid of this invention as well as a composition comprising the AAV capsid protein, AAV capsid and/or virus vector of this invention in a pharmaceutically acceptable carrier.

The present invention additionally provides a method of introducing a nucleic acid into a cell, comprising contacting the cell with the virus vector of this invention. The cell can be in a subject and in some embodiments, the subject can be a human subject.

In some exemplary embodiments, the AAV capsid protein donor can be AAV serotype 9 and the AAV capsid protein template can be AAV serotype 1 (AAV1), AAV serotype 2 (AAV2), AAV serotype 3a (AAV3a), AAV serotype 3b (AAV3b), AAV serotype 4 (AAV4), AAV serotype 5 (AAV5), AAV serotype 6 (AAV6), AAV serotype 7 (AAV7), AAV serotype 8 (AAV8), or AAV serotype 10 (AAV10).

In some exemplary embodiments, the AAV capsid protein template can be from AAV2, and a) the substitution at amino acid 266 is A266S; b) the substitutions at amino acids 463-475 are SQAGASDIRDQSR (SEQ ID NO:1)463-475 $SX_1AGX_2SX_3X_4X_5X_6QX_7R$ (SEQ ID NO:2), wherein $X_{1-7}$ can be any amino acid; and c) the substitutions at amino acids 499-502 are EYSW (SEQ ID NO:3)499-502$EX_8X_9W$ (SEQ ID NO:4), wherein $X_{8-9}$ can be any amino acid. In some embodiments, $X_1$ can be V; $X_2$ can be P; $X_{3-6}$ can be NMAV (SEQ ID NO:5); and $X_7$ can be G, resulting in the sequence SVAGPSNMAVQGR (SEQ ID NO:6). In some embodiments, $X_8$ can be F and $X_9$ can be A, resulting in the sequence EFAW (SEQ ID NO:7).

The example above is provided to demonstrate the substitutions possible for introducing a galactose binding site from an AAV9 donor into an AAV2 template. Table 3 lists several AAV serotypes for which these corresponding amino acids are identified and exemplary substitutions that can be made in each of these serotypes to introduce the galactose binding site of AAV9. What is shown in Table 3 and described in detail herein is that specific amino acid positions are conserved and others are substituted. Where a substitution is shown, the substitution set forth in Table 3 is exemplary of various substitutions that can be made at these residue positions. It is contemplated that the embodiments of this invention encompass other donor AAV serotypes besides AAV9 and other glycan binding sites besides the galactose binding site.

Table 2 lists non-limiting exemplary serotypes of AAV and accession numbers of the genome and capsid sequences that may be encompassed by the invention. The AAV serotype of the donor and the template is not limited to human AAV, but may include non-human AAV, for example, Avian or Bovine AAV, as well as non-human primate AAV, examples of which are shown in Table 1.

The example above shows the possible amino acid substitutions in an AAV2 template for introduction of a galactose binding site from an AAV9 donor. In another example, the template can be AAV1 or AAV6 and the substitutions at the amino acid positions corresponding to positions 463-475 of AAV2 can be $SX_1X_2X_3PX_4X_5MX_6VQX_7X_8$ (SEQ ID NO:8), wherein $X_{1-8}$ can be any amino acid. In a particular embodiment, $X_{1-3}$ is VAG; $X_4$ is S; $X_5$ is N; $X_6$ is A; $X_7$ is G and $X_8$ is R, resulting in the sequence SVAGPSNMAVQGR (SEQ ID NO:6). In further embodiments, substitution at the amino acid positions corresponding to positions 499-502 in AAV2 can be $X_9FX_{10}W$ (SEQ ID NO:9), wherein $X_9$ and $X_{10}$ may be any amino acid. In a particular embodiment, $X_9$ is E and $X_{10}$ is A, resulting in the sequence EFAW (SEQ ID NO:7).

In another example, the template can be AAV3a or AAV3b and the substitutions at the amino acid positions corresponding to positions 463-475 of AAV2 can be $SX_1AGPX_2X_3MX_4X_5QX_6R$ (SEQ ID NO:10) wherein $X_{1-6}$ can be any amino acid. In a particular embodiment, $X_1$ is V; $X_2$ is S; $X_3$ is N; $X_4$ is A; $X_5$ is N; and $X_6$ is G, resulting in the sequence SVAGPSNMAVQGR (SEQ ID NO:6). In further embodiments, substitution at the amino acid positions corresponding to positions 499-502 in AAV2 can be $X_7FX_8W$ (SEQ ID NO:9), wherein $X_7$ and $X_8$ may be any amino acid. In a particular embodiment, $X_7$ is E and $X_8$ is A, resulting in the sequence EFAW (SEQ ID NO:7).

In another example, the template can be AAV4 and the substitutions at the amino acid positions corresponding to positions 463-475 of AAV2 can be $X_1X_2X_3X_4PX_5NX_6X_7X_8X_9X_{10}X_{11}$ (SEQ ID NO:11) wherein $X_{1-11}$ can be any amino acid. In a particular embodiment, $X_1$ is S; $X_2$ is V; $X_3$ is A; $X_4$ is G; $X_5$ is S; $X_6$ is M; $X_7$ is A; $X_8$ is V; $X_9$ is Q; $X_{10}$ is G; and $X_{11}$ is R, resulting in the sequence SVAGPSNMAVQGR (SEQ ID NO:6). In further embodiments, substitution at the amino acid positions corresponding to positions 499-502 in AAV2 can be $X_{12}X_{13}X_{14}X_{15}$ (SEQ ID NO:12), wherein $X_{12-15}$ can be any amino acid. In a particular embodiment, $X_{12}$ is E; $X_{13}$ is F; $X_{14}$ is A; and $X_{15}$ is W, resulting in the sequence EFAW (SEQ ID NO:7).

In another example, the template can be AAV5 and the substitutions at the amino acid positions corresponding to positions 463-475 of AAV2 can be $X_1X_2X_3X_4X_5X_6X_7X_8AX_9X_{10}X_{11}X_{12}$ (SEQ ID NO:13), wherein $X_{1-12}$ can be any amino acid. In a particular embodiment, $X_1$ is S; $X_2$ is V; $X_3$ is A; $X_4$ is G; $X_5$ is P; $X_6$ is S; $X_7$ is N; $X_8$ is M; $X_9$ is V; $X_{10}$ is Q; $X_{12}$ is G; and $X_{12}$ is R, resulting in the sequence SVAGPSNMAVQGR (SEQ ID NO:6). In further embodiments, substitution at the amino acid positions corresponding to positions 499-502 in AAV2 can be $X_{13}X_{14}AX_{15}$ (SEQ ID NO:14), wherein $X_{13-15}$ can be any amino acid. In a particular embodiment, $X_{13}$ is E; $X_{14}$ is F; $X_{15}$ is A; and $X_{16}$ is W, resulting in the sequence EFAW (SEQ ID NO:7).

In another example, the template can be AAV7 and the substitutions at the amino acid positions corresponding to positions 463-475 of AAV2 can be $X_1X_2X_3GPSX_4MAX_5QX_6X_7$ (SEQ ID NO:15), wherein $X_{1-7}$ can be any amino acid. In a particular embodiment, $X_1$ is S; $X_2$ is V; $X_3$ is A; $X_4$ is N; $X_5$ is V; $X_6$ is G; and $X_7$ is R, resulting in the sequence SVAGPSNMAVQGR (SEQ ID NO:6). In further embodiments, substitution at the amino acid positions corresponding to positions 499-502 in AAV2 can be $X_8FAW$ (SEQ ID NO:16), wherein $X_8$ can be any amino acid. In a particular embodiment, wherein $X_8$ is E, resulting in the sequence EFAW (SEQ ID NO:7).

In another example, the template can be AAV8 and the substitutions at the amino acid positions corresponding to positions 463-475 of AAV2 can be $SX_1X_2GPX_3X_4MAX_5QX_6X_7$ (SEQ ID NO:17), wherein $X_{1-7}$ can be any amino acid. In a particular embodiment, $X_1$ is V; $X_2$ is A; $X_3$ is S; $X_4$ is N; $X_5$ is V; $X_6$ is G; and $X_7$ is R, resulting in the sequence SVAGPSNMAVQGR (SEQ ID NO:6). In further embodiments, substitution at the amino acid positions corresponding to positions 499-502 in AAV2 can be $X_8FAW$ (SEQ ID NO:16), wherein $X_8$ can be any amino acid. In a particular embodiment, $X_8$ can be E, resulting in the sequence EFAW (SEQ ID NO:7).

In another example, the template can be AAV10 and the substitutions at the amino acid positions corresponding to positions 463-475 of AAV2 can be $X_1X_2AGPX_3NMX_4X_5QX_6X_7$ (SEQ ID NO:18), wherein $X_{1-7}$ can be any amino acid. In a particular embodiment, $X_1$ is S; $X_2$ is V; $X_3$ is S; $X_4$ is A; $X_5$ is V; $X_6$ is G; and $X_7$ is R, resulting in the sequence SVAGPSNMAVQGR (SEQ ID NO:6). In further embodiments, substitution at the amino acid positions corresponding to positions 499-502 in AAV2 can be $X_8FAW$ (SEQ ID NO:16), wherein $X_8$ can be any amino acid. In a particular embodiment, $X_8$ can be E, resulting in the sequence EFAW (SEQ ID NO:7).

The examples above describe introduction of a galactose binding site from AAV9 into a capsid protein template that can be AAV2, AAV3a, AAV3b, AAV4, AAV5, AAV7, AAV8 or AAV10. These examples, which are not intended to be limiting, demonstrate this universal principle that a glycan binding site from a donor AAV serotype can be introduced into a capsid protein template of a different AAV serotype (e.g., as listed in Table 3) by modifying residues the define the "pocket" described herein. Such modified or chimeric capsid proteins comprising a new glycan binding site can be assembled into capsids that make up virus particles that can be used as virus vectors that have the beneficial phenotype of increased cell surface binding and more rapid and enhanced transgene expression in vivo.

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, ovine AAV, Clade F AAV and any other AAV now known or later discovered. See, e.g., BERNARD N. FIELDS et al., VIROLOGY, volume 2, chapter 69 (4th ed., Lippincott-Raven Publishers). A number of relatively new AAV serotypes and clades have been identified (see, e.g., Gao et al. (2004) *J. Virology* 78:6381-6388 and Table 1).

The genomic sequences of various serotypes of AAV, as well as the sequences of the native terminal repeats (TRs), Rep proteins, and capsid subunits are known in the art.

Exemplary but non-limiting examples of such sequences may be found in the literature or in public databases such as GenBank® Database. See, e.g., GenBank® Database Accession Numbers NC_002077.1, NC_001401.2, NC_001729.1, NC_001863.1, NC_001829.1, NC_006152.1, NC_001862.1, AF513851.1, AF513852.1, the disclosures of which are incorporated by reference herein for teaching parvovirus and AAV nucleic acid and amino acid sequences. See also, e.g., Srivistava et al. (1983) *J. Virology* 45:555; Chiorini et al. (1998) *J. Virology* 71:6823; Chiorini et al. (1999) *J. Virology* 73:1309; Bantel-Schaal et al. (1999) *J. Virology* 73:939; Xiao et al. (1999) *J. Virology* 73:3994; Muramatsu et al. (1996) *Virology* 221:208; Shade et al. (1986) *J. Virol.* 58:921; Gao et al. (2002) *Proc. Nat. Acad. Sci. USA* 99:11854; international patent publications WO 00/28061, WO 99/6160 and WO 98/11244; and U.S. Pat. No. 6,156,303; the disclosures of which are incorporated by reference herein for teaching parvovirus and AAV nucleic acid and amino acid sequences.

The capsid structures of autonomous parvoviruses and AAV are described in more detail in BERNARD N. FIELDS et al., *Virology*, Volume 2, Chapters 69 & 70 (4th ed., Lippincott-Raven Publishers). See also, description of the crystal structure of AAV2 (Xie et al. (2002) *Proc. Nat. Acad. Sci.* 99:10405-10), AAV4 (Padron et al. (2005) *J Virol.* 79: 5047-58), AAV5 (Walters et al. (2004) *J. Virol.* 78: 3361-71) and CPV (Xie et al. (1996) *J. Biol.* 6:497-520 and Tsao et al. (1991) *Science* 251: 1456-64).

Definitions

The singular forms "a," "an" and "the" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

As used herein, the terms "reduce," "reduces," "reduction" and similar terms mean a decrease of at least about 5%, 10%, 15%, 20%, 25%, 35%, 50%, 75%, 80%, 85%, 90%, 95%, 97%, 98%, 99%, 100% or more.

As used herein, the terms "enhance," "enhances," "enhancement" and similar terms indicate an increase of at least about 10%, 20%, 25%, 50%, 75%, 100%, 150%, 200%, 300%, 400%, 500% or more.

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide), but in representative embodiments are either single or double stranded DNA sequences.

As used herein, an "isolated" polynucleotide (e.g., an "isolated DNA" or an "isolated RNA") means a polynucleotide at least partially separated from at least some of the other components of the naturally occurring organism or virus, for example, the cell or viral structural components or other polypeptides or nucleic acids commonly found associated with the polynucleotide. In representative embodiments an "isolated" nucleotide is enriched by at least about 10-fold, 100-fold, 1000-fold, 10,000-fold or more as compared with the starting material.

Likewise, an "isolated" polypeptide means a polypeptide that is at least partially separated from at least some of the other components of the naturally occurring organism or virus, for example, the cell or viral structural components or other polypeptides or nucleic acids commonly found associated with the polypeptide. In representative embodiments an "isolated" polypeptide is enriched by at least about 10-fold, 100-fold, 1000-fold, 10,000-fold or more as compared with the starting material.

As used herein, by "isolate" or "purify" (or grammatical equivalents) a virus vector, it is meant that the virus vector is at least partially separated from at least some of the other components in the starting material. In representative embodiments an "isolated" or "purified" virus vector is enriched by at least about 10-fold, 100-fold, 1000-fold, 10,000-fold or more as compared with the starting material.

A "therapeutic polypeptide" is a polypeptide that can alleviate, reduce, prevent, delay and/or stabilize symptoms that result from an absence or defect in a protein in a cell or subject and/or is a polypeptide that otherwise confers a benefit to a subject, e.g., anti-cancer effects or improvement in transplant survivability.

By the terms "treat," "treating" or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing" and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" or "effective" amount as used herein is an amount that is sufficient to provide some improvement or benefit to the subject. Alternatively stated, a "treatment effective" or "effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "heterologous nucleotide sequence" and "heterologous nucleic acid" are used interchangeably herein and refer to a sequence that is not naturally occurring in the virus. Generally, the heterologous nucleic acid comprises an open reading frame that encodes a polypeptide or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone.

The virus vectors of the invention can further be "targeted" virus vectors (e.g., having a directed tropism) and/or a "hybrid" parvovirus (i.e., in which the viral TRs and viral capsid are from different parvoviruses) as described in international patent publication WO 00/28004 and Chao et al. (2000) *Molecular Therapy* 2:619.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged into the virus capsids of the invention.

Methods of Producing Virus Vectors.

The invention also encompasses virus vectors comprising the modified capsid proteins and capsids of the invention. In particular embodiments, the virus vector is a parvovirus vector (e.g., comprising a parvovirus capsid and/or vector genome), for example, an AAV vector (e.g., comprising an AAV capsid and/or vector genome). In representative embodiments, the virus vector comprises a modified AAV capsid comprising a modified capsid subunit of the invention and a vector genome.

For example, in representative embodiments, the virus vector comprises: (a) a modified virus capsid (e.g., a modified AAV capsid) comprising a modified capsid protein of the invention; and (b) a nucleic acid comprising a terminal repeat sequence (e.g., an AAV TR), wherein the nucleic acid comprising the terminal repeat sequence is encapsidated by the modified virus capsid. The nucleic acid can optionally comprise two terminal repeats (e.g., two AAV TRs).

In representative embodiments, the virus vector is a recombinant virus vector comprising a heterologous nucleic acid encoding a polypeptide or functional RNA of interest. Recombinant virus vectors are described in more detail below.

In particular embodiments, the virus vectors of the invention have reduced transduction of liver as compared with the level of transduction by a virus vector without the modified capsid protein. In particular embodiments, the virus vector has systemic transduction toward muscle, e.g., the vector transduces multiple skeletal muscle groups throughout the body and optionally transduces cardiac muscle and/or diaphragm muscle.

It will be understood by those skilled in the art that the modified capsid proteins, virus capsids and virus vectors of the invention exclude those capsid proteins, capsids and virus vectors that have the indicated amino acids at the specified positions in their native state (i.e., are not mutants).

The present invention further provides methods of producing the inventive virus vectors. In one representative embodiment, the present invention provides a method of producing a virus vector, the method comprising providing to a cell: (a) a nucleic acid template comprising at least one TR sequence (e.g., AAV TR sequence), and (b) AAV sequences sufficient for replication of the nucleic acid template and encapsidation into AAV capsids (e.g., AAV rep sequences and AAV cap sequences encoding the AAV capsids of the invention). Optionally, the nucleic acid template further comprises at least one heterologous nucleic acid sequence. In particular embodiments, the nucleic acid template comprises two AAV ITR sequences, which are located 5' and 3' to the heterologous nucleic acid sequence (if present), although they need not be directly contiguous thereto.

The nucleic acid template and AAV rep and cap sequences are provided under conditions such that virus vector comprising the nucleic acid template packaged within the AAV capsid is produced in the cell. The method can further comprise the step of collecting the virus vector from the cell. The virus vector can be collected from the medium and/or by lysing the cells.

The cell can be a cell that is permissive for AAV viral replication. Any suitable cell known in the art may be employed. In particular embodiments, the cell is a mammalian cell. As another option, the cell can be a trans-complementing packaging cell line that provides functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski (1992) *Curr. Top. Microbiol. Immun.* 158:67).

As a further alternative, the rep/cap sequences may be stably incorporated into a cell.

Typically the AAV rep/cap sequences will not be flanked by the TRs, to prevent rescue and/or packaging of these sequences.

The nucleic acid template can be provided to the cell using any method known in the art. For example, the template can be supplied by a non-viral (e.g., plasmid) or viral vector. In particular embodiments, the nucleic acid template is supplied by a herpesvirus or adenovirus vector (e.g., inserted into the E1a or E3 regions of a deleted adenovirus). As another illustration, Palombo et al. (1998) *J. Virology* 72:5025, describes a baculovirus vector carrying a reporter gene flanked by the AAV TRs. EBV vectors may also be employed to deliver the template, as described above with respect to the rep/cap genes.

In another representative embodiment, the nucleic acid template is provided by a replicating rAAV virus. In still other embodiments, an AAV provirus comprising the nucleic acid template is stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient AAV production as described by Ferrari et al. (1997) Nature Med. 3:1295; and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by TRs.

Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector can further comprise the nucleic acid template. The AAV rep/cap sequences and/or the rAAV template can be inserted into a deleted region (e.g., the E1a or E3 regions) of the adenovirus.

In a further embodiment, the AAV rep/cap sequences and the adenovirus helper sequences are supplied by a single adenovirus helper vector. According to this embodiment, the rAAV template can be provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The rAAV template can be provided as a separate replicating viral vector. For example, the rAAV template can be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids. As described above, the adenovirus helper sequences and the AAV rep/cap sequences are generally not flanked by TRs so that these sequences are not packaged into the AAV virions.

Zhang et al. ((2001) Gene Ther. 18:704-12) describes a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al. (1999) Gene Therapy 6:986 and PCT Publication No. WO 00/17377.

As a further alternative, the virus vectors of the invention can be produced in insect cells using baculovirus vectors to deliver the rep/cap genes and rAAV template as described, for example, in Urabe et al. (2002) Human Gene Therapy 13:1935-43.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) Gene Therapy 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

Recombinant Virus Vectors.

The virus vectors of the present invention are useful for the delivery of nucleic acids to cells in vitro, ex vivo, and in vivo. In particular, the virus vectors can be advantageously employed to deliver or transfer nucleic acids to animal cells, including e.g., mammalian cells.

Any heterologous nucleic acid sequence(s) of interest may be delivered in the virus vectors of the present invention. Nucleic acids of interest include nucleic acids encoding polypeptides, including therapeutic (e.g., for medical or veterinary uses) or immunogenic (e.g., for vaccines) polypeptides.

Therapeutic polypeptides include, but are not limited to, cystic fibrosis transmembrane regulator protein (CFTR), dystrophin (including mini- and micro-dystrophins, see, e.g., Vincent et al. (1993) Nature Genetics 5:130; U.S. Patent Publication No. 2003017131; PCT Publication No. WO/2008/088895, Wang et al. Proc. Natl. Acad. Sci. USA 97:13714-13719 (2000); and Gregorevic et al. Mol. Ther. 16:657-64 (2008)), myostatin propeptide, follistatin, activin type II soluble receptor, IGF-1, anti-inflammatory polypeptides such as the I kappa B dominant mutant, sarcospan, utrophin (Tinsley et al. (1996) Nature 384:349), mini-utrophin, clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, ornithine transcarbamylase, β-globin, α-globin, spectrin, $\alpha_1$-antitrypsin, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, cytokines (e.g., α-interferon, β-interferon, interferon-α, interleukin-2, interleukin-4, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor-3 and -4, brain-derived neurotrophic factor, bone morphogenic proteins [including RANKL and VEGF], glial derived growth factor, transforming growth factor-α and -β, and the like), lysosomal acid α-glucosidase, α-galactosidase A, receptors (e.g., the tumor necrosis growth factorα soluble receptor), S100A1, parvalbumin, adenylyl cyclase type 6, a molecule that modulates calcium handling (e.g., SERCA$_{2A}$, Inhibitor 1 of PP1 and fragments thereof [e.g., PCT Publication Nos. WO 2006/029319 and WO 2007/100465]), a molecule that effects G-protein coupled receptor kinase type 2 knockdown such as a truncated constitutively active bARKct, anti-inflammatory factors such as IRAP, anti-myostatin proteins, aspartoacylase, monoclonal antibodies (including single chain monoclonal antibodies; an exemplary Mab being the HERCEPTIN® Mab), neuropeptides and fragments thereof (e.g., galanin, Neuropeptide Y (see U.S. Pat. No. 7,071,172), angiogenesis inhibitors such as Vasohibins and other VEGF inhibitors (e.g., Vasohibin 2 [see PCT Publication WO JP2006/073052]). Other illustrative heterologous nucleic acid sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof. AAV vectors can also be used to deliver monoclonal antibodies and antibody fragments, for example, an antibody or antibody fragment directed against myostatin (see, e.g., Fang et al. *Nature Biotechnology* 23:584-590 (2005)).

Heterologous nucleic acid sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Optionally, the heterologous nucleic acid encodes a secreted polypeptide (e.g., a polypeptide that is a secreted polypeptide in its native state or that has been engineered to be secreted, for example, by operable association with a secretory signal sequence as is known in the art).

Alternatively, in particular embodiments of this invention, the heterologous nucleic acid may encode an antisense nucleic acid, a ribozyme (e.g., as described in U.S. Pat. No. 5,877,022), RNAs that effect spliceosome-mediated transsplicing (see, Puttaraju et al. (1999) *Nature Biotech.* 17:246; U.S. Pat. No. 6,013,487; U.S. Pat. No. 6,083,702), interfering RNAs (RNAi) including siRNA, shRNA or miRNA that mediate gene silencing (see, Sharp et al. (2000) *Science* 287:2431), and other non-translated RNAs, such as "guide" RNAs (Gorman et al. (1998) *Proc. Nat. Acad. Sci. USA* 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see e.g., Andino et al. *J. Gene Med.* 10:132-142 (2008) and Li et al. *Acta Pharmacol Sin.* 26:51-55 (2005)); phospholamban inhibitory or dominant-negative molecules such as phospholamban S16E (e.g., to treat cardiovascular disease, see e.g., Hoshijima et al. *Nat. Med* 8:864-871 (2002)), RNAi to adenosine kinase (e.g., for epilepsy), and RNAi directed against pathogenic organisms and viruses (e.g., hepatitis B and/or C virus, human immunodeficiency virus, CMV, herpes simplex virus, human papilloma virus, etc.).

Further, a nucleic acid sequence that directs alternative splicing can be delivered. To illustrate, an antisense sequence (or other inhibitory sequence) complementary to the 5' and/or 3' splice site of dystrophin exon 51 can be delivered in conjunction with a U1 or U7 small nuclear (sn) RNA promoter to induce skipping of this exon. For example, a DNA sequence comprising a U1 or U7 snRNA promoter located 5' to the antisense/inhibitory sequence(s) can be packaged and delivered in a modified capsid of the invention.

The virus vector may also comprise a heterologous nucleic acid that shares homology with and recombines with a locus on a host chromosome. This approach can be utilized, for example, to correct a genetic defect in the host cell.

The present invention also provides virus vectors that express an immunogenic polypeptide, e.g., for vaccination. The nucleic acid may encode any immunogen of interest known in the art including, but not limited to, immunogens from human immunodeficiency virus (HIV), simian immunodeficiency virus (SIV), influenza virus, HIV or SW gag proteins, tumor antigens, cancer antigens, bacterial antigens, viral antigens, and the like.

The use of parvoviruses as vaccine vectors is known in the art (see, e.g., Miyamura et al., (1994) *Proc. Nat. Acad. Sci USA* 91:8507; U.S. Pat. No. 5,916,563 to Young et al., U.S. Pat. No. 5,905,040 to Mazzara et al., U.S. Pat. No. 5,882,652, U.S. Pat. No. 5,863,541 to Samulski et al.). The antigen may be presented in the parvovirus capsid. Alternatively, the antigen may be expressed from a heterologous nucleic acid introduced into a recombinant vector genome. Any immunogen of interest as described herein and/or as is known in the art can be provided by the virus vector of the present invention.

An immunogenic polypeptide can be any polypeptide suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env gene products). The immunogenic polypeptide can also be an arenavirus immunogen (e.g., Lassa fever virus immunogen, such as the Lassa fever virus nucleocapsid protein and/or the Lassa fever envelope glycoprotein), a poxvirus immunogen (e.g., a vaccinia virus immunogen, such as the vaccinia L1 or L8 gene product), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g, RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogenic polypeptide can further be a polio immunogen, a herpesvirus immunogen (e.g., CMV, EBV, HSV immunogens) a mumps virus immunogen, a measles virus immunogen, a rubella virus immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell. Exemplary cancer and tumor cell antigens are described in S. A. Rosenberg (*Immunity* 10:281 (1991)). Other illustrative cancer and tumor antigens include, but are not limited to: BRCA1 gene product, BRCA2 gene product, gp100, tyrosinase, GAGE-1/2, BAGE, RAGE, LAGE, NY-ESO-1, CDK-4, β-catenin, MUM-1, Caspase-8, KIAA0205, HPVE, SART-1, PRAME, p15, melanoma tumor antigens (Kawakami et al. (1994) *Proc. Natl. Acad. Sci. USA* 91:3515; Kawakami et al. (1994) *J. Exp. Med.*, 180:347; Kawakami et al. (1994) *Cancer Res.* 54:3124), MART-1, gp100 MAGE-1, MAGE-2, MAGE-3, CEA, TRP-1, TRP-2, P-15, tyrosinase (Brichard et al. (1993) *J Exp. Med.* 178: 489); HER-2/neu gene product (U.S. Pat. No. 4,968,603), CA125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) *Ann. Rev. Biochem.* 62:623); mucin antigens (PCT Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified (see, e.g., Rosenberg, (1996) *Ann. Rev. Med.* 47:481-91).

As a further alternative, the heterologous nucleic acid can encode any polypeptide that is desirably produced in a cell in vitro, ex vivo, or in vivo. For example, the virus vectors may be introduced into cultured cells and the expressed gene product isolated therefrom.

It will be understood by those skilled in the art that the heterologous nucleic acid(s) of interest can be operably associated with appropriate control sequences. For example, the heterologous nucleic acid can be operably associated with expression control elements, such as transcription/translation control signals, origins of replication, polyadenylation signals, internal ribosome entry sites (IRES), promoters, and/or enhancers, and the like.

Further, regulated expression of the heterologous nucleic acid(s) of interest can be achieved at the post-transcriptional level, e.g., by regulating selective splicing of different introns by the presence or absence of an oligonucleotide, small molecule and/or other compound that selectively blocks splicing activity at specific sites (e.g., as described in PCT Publication No. WO 2006/119137).

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and/or lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors according to the present invention provide a means for delivering heterologous nucleic acids into a broad range of cells, including dividing and non-dividing cells. The virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors of the present invention can be employed to deliver a heterologous nucleic acid encoding a polypeptide or functional RNA to treat and/or prevent any disease state for which it is beneficial to deliver a therapeutic polypeptide or functional RNA. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (ß-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product, mir-26a [e.g., for hepatocellular carcinoma]), diabetes mellitus (insulin), muscular dystrophies including Duchenne (dystrophin, mini-dystrophin, insulin-like growth factor I, a sarcoglycan [e.g., α, β, γ], RNAi against myostatin, myostatin propeptide, follistatin, activin type II soluble receptor, anti-inflammatory polypeptides such as the Ikappa B dominant mutant, sarcospan, utrophin, mini-utrophin, antisense or RNAi against splice junctions in the dystrophin gene to induce exon skipping [see e.g., PCT Publication No. WO/2003/095647], antisense against U7 snRNAs to induce exon skipping [see e.g., PCT Publication No. WO/2006/021724], and antibodies or antibody fragments against myostatin or myostatin propeptide) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic disorders, congenital emphysema (α1-antitrypsin), Lesch-Nyhan Syndrome (hypoxanthine guanine phosphoribosyl transferase), Niemann-Pick disease (sphingomyelinase), Tays Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration and/or vasohibin or other inhibitors of VEGF or other angiogenesis inhibitors to treat/prevent retinal disorders, e.g., in Type I diabetes), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1) and fragments thereof (e.g., I1C), serca2a, zinc finger proteins that regulate the phospholamban gene, Barkct, β2-adrenergic receptor, β2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as IRAP and TNFα soluble receptor), hepatitis (α-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BNP 2, 7, etc., RANKL and/or VEGF) can be administered with a bone allograft, for example, following a break or surgical removal in a cancer patient.

The invention can also be used to produce induced pluripotent stem cells (iPS). For example, a virus vector of the invention can be used to deliver stem cell associated nucleic acid(s) into a non-pluripotent cell, such as adult fibroblasts, skin cells, liver cells, renal cells, adipose cells, cardiac cells, neural cells, epithelial cells, endothelial cells, and the like. Nucleic acids encoding factors associated with stem cells are known in the art. Nonlimiting examples of such factors associated with stem cells and pluripotency include Oct-3/4, the SOX family (e.g., SOX1, SOX2, SOX3 and/or SOX15), the Klf family (e.g., Klf1, Klf2, Klf4 and/or Klf5), the Myc family (e.g., C-myc, L-myc and/or N-myc), NANOG and/or LIN28.

The invention can also be practiced to treat and/or prevent a metabolic disorder such as diabetes (e.g., insulin), hemophilia (e.g., Factor IX or Factor VIII), a lysosomal storage disorder such as a mucopolysaccharidosis disorder (e.g., Sly syndrome [β-glucuronidase], Hurler Syndrome [α-L-iduronidase], Scheie Syndrome [α-L-iduronidase], Hurler-Scheie Syndrome [α-L-iduronidase], Hunter's Syndrome [iduronate sulfatase], Sanfilippo Syndrome A [heparan sulfamidase], B [N-acetylglucosaminidase], C [acetyl-CoA:α-glucosaminide acetyltransferase], D [N-acetylglucosamine 6-sulfatase], Morquio Syndrome A [galactose-6-sulfate sulfatase], B [β-galactosidase], Maroteaux-Lamy Syndrome [N-acetylgalactosamine-4-sulfatase], etc.), Fabry disease (α-galactosidase), Gaucher's disease (glucocerebrosidase), or a glycogen storage disorder (e.g., Pompe disease; lysosomal acid α-glucosidase).

Gene transfer has substantial potential use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, virus vectors according to the present invention permit the treatment and/or prevention of genetic diseases.

The virus vectors according to the present invention may also be employed to provide a functional RNA to a cell in vitro or in vivo. Expression of the functional RNA in the cell, for example, can diminish expression of a particular target protein by the cell. Accordingly, functional RNA can be administered to decrease expression of a particular protein in a subject in need thereof. Functional RNA can also be administered to cells in vitro to regulate gene expression and/or cell physiology, e.g., to optimize cell or tissue culture systems or in screening methods.

In addition, virus vectors according to the instant invention find use in diagnostic and screening methods, whereby a nucleic acid of interest is transiently or stably expressed in a cell culture system, or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

As a further aspect, the virus vectors of the present invention may be used to produce an immune response in a subject. According to this embodiment, a virus vector comprising a heterologous nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

Alternatively, the virus vector may be administered to a cell ex vivo and the altered cell is administered to the subject. The virus vector comprising the heterologous nucleic acid is introduced into the cell, and the cell is administered to the subject, where the heterologous nucleic acid encoding the immunogen can be expressed and induce an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to an immunogen by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment and/or prevention of disease, in particular cancer or tumors (e.g., by preventing cancer or tumor formation, by causing regression of a cancer or tumor and/or by preventing metastasis and/or by preventing growth of metastatic nodules). The protective effects may be complete or partial, as long as the benefits of the treatment outweigh any disadvantages thereof.

In particular embodiments, the virus vector or cell comprising the heterologous nucleic acid can be administered in an immunogenically effective amount, as described herein.

The virus vectors of the present invention can also be administered for cancer immunotherapy by administration of a virus vector expressing one or more cancer cell antigens (or an immunologically similar molecule) or any other immunogen that produces an immune response against a cancer cell. To illustrate, an immune response can be produced against a cancer cell antigen in a subject by administering a virus vector comprising a heterologous nucleic acid encoding the cancer cell antigen, for example to treat a patient with cancer and/or to prevent cancer from developing in the subject. The virus vector may be administered to a subject in vivo or by using ex vivo methods, as described herein. Alternatively, the cancer antigen can be expressed as part of the virus capsid or be otherwise associated with the virus capsid (e.g., as described above).

As another alternative, any other therapeutic nucleic acid (e.g., RNAi) or polypeptide (e.g., cytokine) known in the art can be administered to treat and/or prevent cancer.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In representative embodiments, the invention provides a method of treating and/or preventing tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In particular embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

In particular embodiments, cells may be removed from a subject with cancer and contacted with a virus vector expressing a cancer cell antigen according to the instant invention. The modified cell is then administered to the subject, whereby an immune response against the cancer cell antigen is elicited. This method can be advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector.

Cytokines may be administered by any method known in the art. Exogenous cytokines may be administered to the subject, or alternatively, a nucleic acid encoding a cytokine may be delivered to the subject using a suitable vector, and the cytokine produced in vivo.

Subjects, Pharmaceutical Formulations, and Modes of Administration.

Virus vectors and capsids according to the present invention find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles, adults and geriatric subjects.

In representative embodiments, the subject is "in need of" the methods of the invention and thus in some embodiments can be a "subject in need thereof."

In particular embodiments, the present invention provides a pharmaceutical composition comprising a virus vector and/or capsid of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, optionally at least about $10^5$ infectious units are introduced to the cell.

The cell(s) into which the virus vector is introduced can be of any type, including but not limited to neural cells (including cells of the peripheral and central nervous systems, in particular, brain cells such as neurons and oligodendricytes), lung cells, cells of the eye (including retinal cells, retinal pigment epithelium, and corneal cells), epithelial cells (e.g., gut and respiratory epithelial cells), muscle cells (e.g., skeletal muscle cells, cardiac muscle cells, smooth muscle cells and/or diaphragm muscle cells), dendritic cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. In representative embodiments, the cell can be any progenitor cell. As a further embodiment, the cell can be a stem cell (e.g., neural stem cell, liver stem cell). As still a further embodiment, the cell can be a cancer or tumor cell. Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo nucleic acid delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

In some embodiments, the virus vector is introduced into a cell and the cell can be administered to a subject to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response against the polypeptide in the subject to which the pharmaceutical formulation is administered. In particular embodiments, the dosage is sufficient to produce a protective immune response (as defined above). The degree of protection conferred need not be complete or permanent, as long as the benefits of administering the immunogenic polypeptide outweigh any disadvantages thereof.

A further aspect of the invention is a method of administering the virus vector and/or virus capsid to a subject. Administration of the virus vectors and/or capsids according to the present invention to a human subject or an animal in need thereof can be by any means known in the art. Optionally, the virus vector and/or capsid can be delivered in a treatment effective or prevention effective dose in a pharmaceutically acceptable carrier.

The virus vectors and/or capsids of the invention can further be administered to elicit an immunogenic response (e.g., as a vaccine). Typically, immunogenic compositions of the present invention comprise an immunogenically effective amount of virus vector and/or capsid in combination with a pharmaceutically acceptable carrier. Optionally, the dosage is sufficient to produce a protective immune response (as defined above).

Dosages of the virus vector and/or capsid to be administered to a subject depend upon the mode of administration, the disease or condition to be treated and/or prevented, the individual subject's condition, the particular virus vector or capsid, the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^3$, $10^{14}$, $10^{15}$ transducing units, optionally about $10^8$-$10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intralymphatic, and the like, as well as direct tissue or organ injection (e.g., to liver, skeletal muscle, cardiac muscle, diaphragm muscle or brain). Administration can also be to a tumor (e.g., in or near a tumor or a lymph node). The most suitable route in any given case will depend on the nature and severity of the condition being treated and/or prevented and on the nature of the particular vector that is being used.

Administration to skeletal muscle according to the present invention includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. Suitable skeletal muscles include but are not limited to abductor digiti minimi (in the hand), abductor digiti minimi (in the foot), abductor hallucis, abductor ossis metatarsi quinti, abductor pollicis *brevis*, abductor pollicis longus, adductor *brevis*, adductor hallucis, adductor longus, adductor magnus, adductor pollicis, anconeus, anterior scalene, articularis genus, biceps brachii, biceps femoris, *brachialis*, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radialis *brevis*, extensor carpi radialis longus, extensor carpi ulnaris, extensor digiti minimi, extensor digitorum, extensor digitorum *brevis*, extensor digitorum longus, extensor hallucis *brevis*, extensor hallucis longus, extensor indicis, extensor pollicis *brevis*, extensor pollicis longus, flexor carpi radialis, flexor carpi ulnaris, flexor digiti minimi *brevis* (in the hand), flexor digiti minimi *brevis* (in the foot), flexor digitorum *brevis*, flexor digitorum longus, flexor digitorum *profundus*, flexor digitorum superficialis, flexor hallucis *brevis*, flexor hallucis longus, flexor pollicis *brevis*, flexor pollicis longus, *frontalis*, gastrocnemius, geniohyoid, gluteus maximus, gluteus medius, gluteus minimus, gracilis, iliocostalis cervicis, iliocostalis lumborum, iliocostalis thoracis, illiacus, inferior gemellus, inferior oblique, inferior rectus, infraspinatus, interspinalis, intertransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the foot), masseter, medial pterygoid, medial rectus, middle scalene, multifidus, mylohyoid, obliquus capitis inferior, obliquus capitis superior, obturator externus, obturator internus, occipitalis, omohyoid, opponens digiti minimi, opponens pollicis, orbicularis oculi, orbicularis oris, palmar interossei, palmaris *brevis*, palmaris longus, pectineus, pectoralis major, pectoralis minor, peroneus *brevis*, peroneus longus, peroneus tertius, *piriformis*, plantar interossei, plantaris, platysma, popliteus, posterior scalene, pronator quadratus, pronator *teres*, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratus anterior, short rotators, soleus, spinalis capitis, spinalis cervicis, spinalis thoracis, splenius capitis, splenius cervicis, sternocleidomastoid, sternohyoid, sternothyroid, stylohyoid, subclavius, subscapularis, superior gemellus, superior oblique, superior rectus, supinator, supraspinatus, temporalis, tensor fascia lata, *teres* major, *teres* minor, thoracis, thyrohyoid, tibialis anterior, tibialis posterior, trapezius, triceps brachii, vastus *intermedius*, vastus lateralis, vastus *medialis*, zygomaticus major, and zygomaticus minor, and any other suitable skeletal muscle as known in the art.

The virus vector and/or capsid can be delivered to skeletal muscle by intravenous administration, intra-arterial administration, intraperitoneal administration, limb perfusion, (optionally, isolated limb perfusion of a leg and/or arm; see e.g. Arruda et al. (2005) *Blood* 105:3458-3464), and/or direct intramuscular injection. In particular embodiments, the virus vector and/or capsid is administered to a limb (arm and/or leg) of a subject (e.g., a subject with muscular dystrophy such as DMD) by limb perfusion, optionally isolated limb perfusion (e.g., by intravenous or intra-articular administration). In embodiments of the invention, the virus vectors and/or capsids of the invention can advantageously be administered without employing "hydrodynamic" techniques. Tissue delivery (e.g., to muscle) of vectors is often enhanced by hydrodynamic techniques (e.g., intravenous/ intravenous administration in a large volume), which increase pressure in the vasculature and facilitate the ability of the vector to cross the endothelial cell barrier. In particular embodiments, the viral vectors and/or capsids of the invention can be administered in the absence of hydrodynamic techniques such as high volume infusions and/or elevated intravascular pressure (e.g., greater than normal systolic pressure, for example, less than or equal to a 5%, 10%, 15%, 20%, 25% increase in intravascular pressure over normal systolic pressure). Such methods may reduce or avoid the side effects associated with hydrodynamic techniques such as edema, nerve damage and/or compartment syndrome.

Administration to cardiac muscle includes administration to the left atrium, right atrium, left ventricle, right ventricle and/or septum. The virus vector and/or capsid can be delivered to cardiac muscle by intravenous administration, intra-arterial administration such as intra-aortic administration, direct cardiac injection (e.g., into left atrium, right atrium, left ventricle, right ventricle), and/or coronary artery perfusion.

Administration to diaphragm muscle can be by any suitable method including intravenous administration, intra-arterial administration, and/or intra-peritoneal administration.

Delivery to a target tissue can also be achieved by delivering a depot comprising the virus vector and/or capsid. In representative embodiments, a depot comprising the virus vector and/or capsid is implanted into skeletal, cardiac and/or diaphragm muscle tissue or the tissue can be contacted with a film or other matrix comprising the virus vector and/or capsid. Such implantable matrices or substrates are described, e.g., in U.S. Pat. No. 7,201,898.

In particular embodiments, a virus vector and/or virus capsid according to the present invention is administered to skeletal muscle, diaphragm muscle and/or cardiac muscle (e.g., to treat and/or prevent muscular dystrophy, heart disease [for example, PAD or congestive heart failure]).

In representative embodiments, the invention is used to treat and/or prevent disorders of skeletal, cardiac and/or diaphragm muscle.

In a representative embodiment, the invention provides a method of treating and/or preventing muscular dystrophy in a subject in need thereof, the method comprising: administering a treatment or prevention effective amount of a virus vector of the invention to a mammalian subject, wherein the virus vector comprises a heterologous nucleic acid encoding dystrophin, a mini-dystrophin, a micro-dystrophin, myostatin propeptide, follistatin, activin type II soluble receptor, IGF-1, anti-inflammatory polypeptides such as the Ikappa B dominant mutant, sarcospan, utrophin, a micro-dystrophin, laminin-α2, α-sarcoglycan, β-sarcoglycan, γ-sarcoglycan, δ-sarcoglycan, IGF-1, an antibody or antibody fragment against myostatin or myostatin propeptide, and/or RNAi against myostatin. In particular embodiments, the virus vector can be administered to skeletal, diaphragm and/or cardiac muscle as described elsewhere herein.

Alternatively, the invention can be practiced to deliver a nucleic acid to skeletal, cardiac or diaphragm muscle, which is used as a platform for production of a polypeptide (e.g., an enzyme) or functional RNA (e.g., RNAi, microRNA, antisense RNA) that normally circulates in the blood or for systemic delivery to other tissues to treat and/or prevent a disorder (e.g., a metabolic disorder, such as diabetes [e.g., insulin], hemophilia [e.g., Factor IX or Factor VIII], a mucopolysaccharide disorder [e.g., Sly syndrome, Hurler Syndrome, Scheie Syndrome, Hurler-Scheie Syndrome, Hunter's Syndrome, Sanfilippo Syndrome A, B, C, D, Morquio Syndrome, Maroteaux-Lamy Syndrome, etc.] or a lysosomal storage disorder such as Gaucher's disease [glucocerebrosidase] or Fabry disease [α-galactosidase A] or a glycogen storage disorder such as Pompe disease [lysosomal acid α glucosidase]). Other suitable proteins for treating and/or preventing metabolic disorders are described herein. The use of muscle as a platform to express a nucleic acid of interest is described in U.S. Patent Publication No. 2002/0192189.

Thus, as one aspect, the invention further encompasses a method of treating and/or preventing a metabolic disorder in a subject in need thereof, the method comprising: administering a treatment or prevention effective amount of a virus vector of the invention to skeletal muscle of a subject, wherein the virus vector comprises a heterologous nucleic acid encoding a polypeptide, wherein the metabolic disorder is a result of a deficiency and/or defect in the polypeptide. Illustrative metabolic disorders and heterologous nucleic acids encoding polypeptides are described herein. Optionally, the polypeptide is secreted (e.g., a polypeptide that is a secreted polypeptide in its native state or that has been engineered to be secreted, for example, by operable association with a secretory signal sequence as is known in the art). Without being limited by any particular theory of the invention, according to this embodiment, administration to the skeletal muscle can result in secretion of the polypeptide into the systemic circulation and delivery to target tissue(s). Methods of delivering virus vectors to skeletal muscle are described in more detail herein.

The invention can also be practiced to produce antisense RNA, RNAi or other functional RNA (e.g., a ribozyme) for systemic delivery.

The invention also provides a method of treating and/or preventing congenital heart failure or PAD in a subject in need thereof, the method comprising administering a treatment or prevention effective amount of a virus vector of the invention to a mammalian subject, wherein the virus vector comprises a heterologous nucleic acid encoding, for example, a sarcoplasmic endoreticulum $Ca^{2+}$-ATPase (SERCA2a), an angiogenic factor, phosphatase inhibitor I (I-1) and fragments thereof (e.g., I1C), RNAi against phospholamban; a phospholamban inhibitory or dominant-negative molecule such as phospholamban S16E, a zinc finger protein that regulates the phospholamban gene, β2-adrenergic receptor, β2-adrenergic receptor kinase (BARK), PI3 kinase, calsarcan, a β-adrenergic receptor kinase inhibitor (βARKct), inhibitor 1 of protein phosphatase 1 and fragments thereof (e.g., I1C), S100A1, parvalbumin, adenylyl cyclase type 6, a molecule that effects G-protein coupled receptor kinase type 2 knockdown such as a truncated constitutively active bARKct, Pim-1, PGC-1α, SOD-1, SOD-2, EC-SOD, kallikrein, HIF, thymosin-β4, mir-1, mir-133, mir-206, mir-208 and/or mir-26a.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local rather than systemic manner, for example, in a depot or sustained-release formulation. Further, the virus vector and/or virus capsid can be delivered adhered to a surgically implantable matrix (e.g., as described in U.S. Patent Publication No. 20040013645).

The virus vectors and/or virus capsids disclosed herein can be administered to the lungs of a subject by any suitable means, optionally by administering an aerosol suspension of respirable particles comprised of the virus vectors and/or virus capsids, which the subject inhales. The respirable particles can be liquid or solid. Aerosols of liquid particles comprising the virus vectors and/or virus capsids may be produced by any suitable means, such as with a pressure-driven aerosol nebulizer or an ultrasonic nebulizer, as is known to those of skill in the art. See e.g., U.S. Pat. No. 4,501,729. Aerosols of solid particles comprising the virus vectors and/or capsids may likewise be produced with any solid particulate medicament aerosol generator, by techniques known in the pharmaceutical art.

The virus vectors and virus capsids can be administered to tissues of the central nervous system (CNS) (e.g., brain, eye) and may advantageously result in broader distribution of the virus vector or capsid than would be observed in the absence of the present invention.

In particular embodiments, the delivery vectors of the invention may be administered to treat diseases of the CNS, including genetic disorders, neurodegenerative disorders, psychiatric disorders and tumors. Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease, Lesch-Nyan disease, epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The delivery vectors of the present invention can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly.

Uveitis involves inflammation. One or more anti-inflammatory factors can be administered by intraocular (e.g., vitreous or anterior chamber) administration of a delivery vector of the invention.

Retinitis pigmentosa, by comparison, is characterized by retinal degeneration. In representative embodiments, retinitis pigmentosa can be treated by intraocular (e.g., vitreal administration) of a delivery vector encoding one or more neurotrophic factors.

Age-related macular degeneration involves both angiogenesis and retinal degeneration. This disorder can be treated by administering the inventive delivery vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, optionally intravitreally.

In other embodiments, the present invention may be used to treat seizures, e.g., to reduce the onset, incidence and/or severity of seizures. The efficacy of a therapeutic treatment for seizures can be assessed by behavioral (e.g., shaking, ticks of the eye or mouth) and/or electrographic means (most seizures have signature electrographic abnormalities). Thus, the invention can also be used to treat epilepsy, which is marked by multiple seizures over time.

In one representative embodiment, somatostatin (or an active fragment thereof) is administered to the brain using a delivery vector of the invention to treat a pituitary tumor. According to this embodiment, the delivery vector encoding somatostatin (or an active fragment thereof) is administered by microinfusion into the pituitary. Likewise, such treatment can be used to treat acromegaly (abnormal growth hormone secretion from the pituitary). The nucleic acid sequences (e.g., GenBank Accession No. J00306) and amino acid sequences (e.g., GenBank Accession No. P01166; contains processed active peptides somatostatin-28 and somatostatin-14) of somatostatins are known in the art.

In particular embodiments, the vector can comprise a secretory signal as described, e.g., in U.S. Pat. No. 7,071, 172.

In representative embodiments of the invention, the virus vector and/or virus capsid is administered to the CNS (e.g., to the brain or to the eye). The virus vector and/or capsid may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and portaamygdala), limbic system, neocortex, corpus striatum, cerebrum, and/or inferior colliculus. The virus vector and/or capsid may also be administered to different regions of the eye such as the retina, cornea and/or optic nerve.

The virus vector and/or capsid may be delivered into the cerebrospinal fluid (e.g., by lumbar puncture) for more disperse administration of the delivery vector. The virus vector and/or capsid may further be administered intravascularly to the CNS in situations in which the blood-brain barrier has been perturbed (e.g., brain tumor or cerebral infarct).

The virus vector and/or capsid can be administered to the desired region(s) of the CNS by any route known in the art, including but not limited to, intrathecal, intracerebral, intraventricular, intravenous (e.g., in the presence of a sugar such as mannitol), intranasal, intra-aural, intra-ocular (e.g., intravitreous, sub-retinal, anterior chamber) and peri-ocular (e.g., sub-Tenon's region) delivery as well as intramuscular delivery with retrograde delivery to motor neurons.

In particular embodiments, the virus vector and/or capsid is administered in a liquid formulation by direct injection (e.g., stereotactic injection) to the desired region or compartment in the CNS. In other embodiments, the virus vector and/or capsid may be provided by topical application to the desired region or by intra-nasal administration of an aerosol formulation. Administration to the eye may be by topical application of liquid droplets. As a further alternative, the virus vector and/or capsid may be administered as a solid, slow-release formulation (see, e.g., U.S. Pat. No. 7,201, 898).

In yet additional embodiments, the virus vector can used for retrograde transport to treat and/or prevent diseases and disorders involving motor neurons (e.g., amyotrophic lateral sclerosis (ALS); spinal muscular atrophy (SMA), etc.). For example, the virus vector can be delivered to muscle tissue from which it can migrate into neurons.

Having described the present invention, the same will be explained in greater detail in the following examples, which are included herein for illustration purposes only and are not intended to be limiting to the invention.

EXAMPLES: ENGINEERING OF DUAL GLYCAN BINDING AAV

Structural Modeling.

Coordinates for the AAV2 and AAV9 viral protein (VP) crystal structures were obtained from RCSB Protein Databank (PDB accession#1LP3 and 3UX1, respectively)[30,31]. Using the SWISS-MODEL protein structure modeling server (http://swissmodel.expasy.org/)[32], homology models of the 2G9 VP3 monomer were generated_ with crystal structures of AAV2 VP3 as template. A three-dimensional icosahedral model of an intact 2G9 capsid was created using the Oligomer Generator utility in VIPERdb-Virus Particle ExploreR2[33]. Similarly, illustration of the AAV2 VP3 trimer, 2G9 trimer, and AAV9 trimer were obtained using the Oligomer Generator utility. All structural models were visualized using PyMOL with residues forming the galactose binding site (AAV9 VP1 numbering: D271, N272, Y446, N470, A472, V473, W503)[13] and heparan sulfate binding site (AAV2 VP1 numbering: R487, K527, K532, R585, R588)[10-12,34] highlighted in orange and purple, respectively. Different monomers were colored in pale green, light blue and light pink.

Generation of Dual Glycan Binding AAV Strains.

Helper plasmids pXR1, 2, 6, 8 and 9 were obtained from UNC vector core. The prototypical pXR2G9 chimera plasmid construct was generated by substituting amino acid residues directly involved or flanking the Gal recognition site on the AAV9 capsid protein subunit onto corresponding residues on the capsid subunit of AAV2 (AAV2 VP1 numbering: A266S, Q464V, A467P, D469N, I470M, R471A, •D472V, S474G, Y500F, S501A). Substitutions were generated using the QUIKCHANGE® Lightning site-directed mutagenesis kit (Agilent) using the following primers (IDT): 5'-GGAACCACCA CGCAGTCAAG GCTTCA-GTTT TCTGTGGCCG GACCCAGTAA CATGGCTGTC CAGGGAAGGA ACTGGCTTCCT GGACCCTGTT ACCGC-3' (SEQ ID NO:19) and 5'-GACATCTGCG GATAACAACA ACAGTGAATTT GCTTGGACTG GAGCTACCAA GTACCACCT-3' (SEQ ID NO:20). Recombinant AAV vectors packaging the CBA-Luc transgene cassettes were generated as described previously[14]. Viral titers were obtained by quantitative PCR.

In vitro binding, transduction and competitive inhibition assays. CHO Lec2 cells were cultured in αMEM (Thermo Scientific) supplemented with 10% fetal bovine serum (FBS), 100 U/ml of penicillin (Cellgro), 100 µg/ml of streptomycin (Cellgro), and 2.5 µg/ml of amphotericin B (Sigma). Cells were seeded at a density of 1×10⁵ cells/well in 24 well plates. For competitive inhibition assays, cells were pre-chilled at 4° C. for 30 minutes and incubated with 100 µg/ml of FITC-labeled *Erythrina Cristagalli* Lectin (FITC-ECL, Vector Labs) in αMEM at 4° C. for 1 hour. Alternatively, different viral capsids were incubated with 100 µg/ml of soluble heparin (Sigma) or 1×PBS (control) at room temperature for 1 hour. Mock-treated or FITC-ECL treated cells were then infected with HS-bound or mock-treated AAV2, AAV2G9, or AAV9 capsids packaging a CBA-Luc transgene cassette at an MOI of 1000 vector genome (vg) copies/cell. Following incubation in the cold room for 1 hour, unbound virions were removed by three washes with ice cold 1×PBS. For cell surface binding assays, the number of bound virions was measured by quantifying vector genome copy numbers/cell in each well using quantitative PCR. For transduction assays, infected Lec2 cells were moved to 37° C. and incubated for 24 hours prior to quantitation of luciferase transgene expression from cell lysates.

For competitive inhibition with parental AAV2 or AAV9 capsids, vectors packaging CBA promoter-driven tdTomato transgene cassette were utilized. Briefly, Lec2 cells were seeded in 24 well plates overnight at a density of 1×10⁵ cells/well. After being pre-chilled at 4° C. for 30 minutes, Lec2 cells were pre-incubated with either AAV2-tdTomato or AAV9-tdTomato vectors at multiplicities of infection (MOI) ranging from 500 to 100,000 vg/cell at 4° C. for another 30 minutes. Cells were then super-infected with AAV2G9-CBA-Luc at an MOI of 1000 vg/cell for 45 minutes at 4° C., followed by removal of unbound virions using ice cold PBS. Infected cells were then incubated at 37° C. for 24 hours prior to luciferase expression analysis. Controls included AAV2-CBA-Luc or AAV9-CBA-Luc vectors.

Kinetics of Transgene Expression In Vivo.

Female BALB/c mice (6-8 weeks old) were purchased from Jackson Laboratories and handled in accordance with NIH guidelines using IACUC approved protocols at UNC Chapel Hill. Different AAV vectors packaging the CBA-Luc cassette were injected intravenously into the tail vein at a dose of 1×10¹¹ vg/mouse. At indicated time intervals post-administration (3, 7, and 18 days), mice were intraperitoneally injected with luciferin (120 mg/kg; Nanolight) and bioluminescent images obtained using a Xenogen IVIS® Lumina system (Caliper Lifesciences). Quantitation of light output from liver and whole animal images was carried out using WAVEMETRICS® software. Further quantitation of luciferase transgene expression and vector genome biodistribution in different tissues was carried out in two different groups of mice that were sacrificed at days 3 and 18 post-vector administration. Luciferase transgene expression was monitored in different tissue lysates as described earlier. Vector genome biodistribution was determined by first extracting genomic DNA from tissue lysates using a DNeasy® Kit (Qiagen). Luciferase transgene copy number was determined using qPCR and normalized to the number of copies of the mouse lamin gene to determine vg/cell in each tissue. Specific primer sets were 5'-AGGGCACCTC CATCTCGGAA AC-3' (SEQ ID NO:21)/5'-GGAC-CCAAGG ACTACCTCAA GGG-3' (SEQ ID NO:22, for mouse lamin) and 5'-AAAAGCACTC TGATTGACAA ATAC-3' (SEQ ID NO:23)/5'-CCTTCGCTTC AAAAAATGGA AC-3' (SEQ ID NO:24, for CBA-Luc), respectively.

Statistical Analysis.

All data is expressed as mean±standard error mean and the number of replicates for each experiment is provided in the corresponding figure legends. Statistical significance was determined using the unpaired one-tail student's t-test and p-values less than 0.05 considered statistically significant for different experiments unless indicated otherwise.

Results

To explore the feasibility of "grafting" the Gal footprint of AAV9 onto several AAV strains, we first compared the three-dimensional structures of VP3 subunit trimers of AAV serotypes 1, 2, 6 and 8 in alignment with that of AAV9 (FIG. 1). Amino acid residues on the template capsids that overlapped with corresponding AAV9 VP3 residues directly involved in binding or immediately flanking the Gal receptor footprint were modified by multiple rounds of site-directed mutagenesis. All of the chimeric AAV strains generated were prepared as recombinant vectors packaging a chicken beta-actin promoter driven firefly luciferase (CBA-Luc) reporter transgene cassette using previously established protocols[14]. Amino acid residues involved in Gal recognition and other flanking residues from AAV9 were remarkably well tolerated on different AAV serotype capsids as the packaging efficiencies of these AAV chimeras are comparable with parental strains. Multiple AAV chimeras based on AAV serotypes 1, 2, 6, 8 and the previously engineered AAV2i8 mutant[15] were obtained (at titers ranging from 5×10¹¹ to 5×10¹² viral genome copies/mL) and observed to exploit Gal as a novel primary receptor in transducing CHO Lec2 cells in vitro (FIG. 2). We then carried out a detailed characterization of a prototypical dual glycan binding AAV chimera, dubbed AAV2G9 (where G stands for the Gal footprint and the numbers identify the recipient and donor capsid serotypes, respectively).

Three-dimensional models of synthetically engineered AAV2G9 (full capsid in FIG. 3, Panel A and VP3 trimer in FIG. 3, Panel D) with the putative dual glycan receptor binding sites (HS and Gal) highlighted were generated by homology modeling using SWISS MODEL® software. The molecular model of AAV2G9 full capsids demonstrates the geometrical distribution and orthogonality of HS and Gal binding sites located around the three-fold symmetry axis on the icosahedral capsid. Close-up views of HS and Gal receptor footprints from the three-fold axes further support the observation that grafting orthogonal Gal binding sites on the backbone of AAV2 capsid can be tolerated with regard to capsid assembly. Three-dimensional structures of the AAV2 VP3 subunit trimer with side chains of positively charged residues involved in HS recognition (FIG. 3, Panel A) as well as the side chains of amino acid residues comprising the Gal recognition site on the AAV9 VP3 subunit trimer (FIG. 3, Panel C) are also shown.

AAV2G9 Exploits HS and Gal Receptors Interchangeably In Vitro.

The first line of evidence supporting the usage of dual glycan receptors by AAV2G9 was obtained from competitive inhibition assays of virus binding on cell surface involving soluble heparin and *Erythrina Cristagalli* lectin (ECL), which selectively binds terminally galactosylated glycans. As seen in FIG. 4, Panels A-B, HS, but not ECL significantly inhibits AAV2 transduction in CHO Lec2 cells (dark grey bars), while ECL selectively blocks AAV9 transduction by nearly two log units (white bars). These results are consistent with the expected transduction profiles for AAV2 and AAV9[16-18]. In contrast, AAV2G9 can only be effectively neutralized by pre-treatment with a combination of both ECL and HS (light grey bars, FIG. 4, Panel C). A small, yet significant inhibitory effect is observed for ECL.

Transduction profiles for AAV2 and AAV9 were further corroborated by inhibition of cell surface binding by each strain using ECL or HS (FIG. 4, Panels D-E). The unique cell surface attachment of the chimeric AAV strain is further supported by competitive inhibition of cell surface attachment of AAV2G9 exclusively by a combination of ECL and HS, but neither reagent alone (FIG. 4, Panel F). In addition, confocal immunofluorescence micrographs (FIG. 5) obtained using monoclonal antibodies against different AAV capsids suggest that AAV2G9 binds more robustly to the surface of CHO Lec2 cells than AAV2 or AAV9. Such a scenario can be expected based on the apparent ability of AAV2G9 to bind two different glycans interchangeably.

In order to further interrogate the exploitation of alternate transduction pathways by AAV2G9, we conducted competition assays with the parental serotypes, AAV2 and AAV9. As shown in FIG. 6, Panels A-B, pre-incubation with AAV2-CBA-tdTom or AAV9-CBA-tdTom competing vectors at MOIs ranging from 500 to 100,000 vg/cell efficiently blocks transduction by AAV2-CBA-Luc or AAV9-CBA-Luc, respectively as measured by luciferase transgene expression. However, both AAV2 and AAV9 are unable to effectively block AAV2G9 transduction at 10-fold excess multiplicities of infection (MOI). At higher MOI (100-fold excess), AAV2 appears to compete less effectively than AAV9 in neutralizing AAV2G9 transduction. Taken together, these results support the notion that AAV2G9 is indeed a novel, dual glycan binding strain with the unique ability to exploit both HS and Gal as primary receptors for transduction.

AAV2G9 Mediates Rapid Onset of Transgene Expression.

We then investigated whether dual glycan binding confers specific advantages to viral transduction in vitro and in vivo. Monitoring the time course of luciferase reporter expression in CHO Lec2 cells revealed that AAV2G9 mediates rapid onset and improved gene transfer in vitro (FIG. 7). Live animal imaging studies were then carried out to monitor luciferase transgene expression following systemic administration of different AAV strains in BALB/c mice (FIG. 8, Panel A). Bioluminescent images and quantitative assessment of light output within the liver and the whole animal obtained at days 3, 7 and 18 post-injection correlate with in vitro data and support the notion that AAV2G9 can mediate rapid onset and enhanced gene expression (FIG. 8, Panels B-C). Interestingly, the kinetic profile displayed by AAV2G9 mirrors that of AAV9 but not AAV2. In contrast, the transduction profile/tissue tropism of AAV2G9 appears to be primarily hepatotropic, similar to AAV2 and unlike the systemic tropism displayed by AAV9 as established previously[4,19-21]. Thus, dual glycan receptor engagement appears to improve the transduction efficiency of AAV strains, but does not alter tissue tropism.

Transduction and Biodistribution Profile of AAV2G9 Vectors In Vivo.

To further evaluate the in vivo transduction and biodistribution profiles of AAV2G9, quantitative analysis of tissue lysates from BALB/c mice were carried out at days 3 and 18 post-administration. Specifically, AAV2G9 displays markedly higher luciferase transgene expression in liver compared to AAV2 (nearly two log units) and AAV9 (~1 log unit) at 3 days post-administration (FIG. 9, Panel A). While AAV9 displays more than 10-fold higher transduction efficiency in heart than AAV2G9, a modest increase in cardiac transduction by AAV2G9 compared to AAV2 is also observed. At day 18, cardiac and liver tissues harvested from mice treated with AAV2G9 continue to demonstrate higher transgene expression, although AAV9 emerges as the most efficient strain at this stage. Specifically, transduction efficiencies in cardiac tissue by AAV2, AAV2G9, and AAV9 maintain a similar trend as observed 3 days post-administration. In the liver, the differences between luciferase transgene expression by AAV2, AAV2G9, and AAV9 diminish upon progressing to 18 days post-injection. Specifically, AAV9 demonstrates between 5 to 10-fold higher transgene expression when compared to AAV2G9 and AAV2, respectively.

Quantitative analysis of vector genome copy numbers in liver and heart by AAV2G9 and the parental AAV strains at 3 days post-administration (FIG. 9, Panel B) is consistent with the trends observed for transduction efficiencies shown in FIG. 5, Panel A. Specifically, AAV2G9 accumulated to a higher extent in cardiac tissue compared to AAV2, but was still ~2 log units lower than AAV9. In liver, AAV2G9 copy number is comparable to that of AAV9, but over one log unit higher than AAV2. At day 18, copy numbers for all serotypes were decreased presumably due to continuous cell turnover and degradation of single-stranded AAV genomes as reported previously[22,23].

FIG. 10 shows in vivo transgene expression kinetics of AAV2i8, 2i8G9, and AAV9 vectors packaging CBA-luciferase transgene cassette. BALB/c mice (n=4) were administered AAV vectors at a dose of $1\times10^{11}$ vg/animal through the tail vein and bioluminescence images were collected at 3, 7, and 18 days post-injection using a XENOGEN® Lumina imaging system. Representative live animal images are shown with bioluminescence expressed on a rainbow colored scale ($10^5$-$10^6$ photons/second/cm²/steradian).

FIG. 11 shows central nervous system (CNS) tropism profiles of representative AAV G9 strains in neonatal mice. Postnatal 0 (P0) pups (n=3) were unilaterally injected into the left cerebral ventricle with 3.5×10e9 AAV vector genomes containing a GFP transgene driven by a hybrid chicken beta actin (CBh) promoter. At 2 wks post injection, GFP immunohistochemistry revealed differential spread, regional and cellular tropisms for each AAV "G9" strain within the murine brain.

The foregoing is illustrative of the present invention, and is not to be construed as limiting thereof.

TABLE 1

AAV Genomes

| Table 1 | GenBank ® Accession Number |
|---|---|
| Complete Genomes | |
| AAV1 | NC_002077, AF063497 |
| AAV2 | NC_001401 |
| AAV 3 | NC_001729 |
| AAV3B | NC_001863 |
| AAV4 | NC_001829 |
| AAV5 | Y18065, AF085716 |
| AAV6 | NC_001862 |
| AAV | AY186198, AY629583, NC_004828 |
| Avian AAV strain DA-1 | NC_006263, AY629583 |
| Bovine AAV | NC_005889, AY388617 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| CY5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |
| Clonal Isolate | |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |

TABLE 2

| Exemplary AAV Genome and Capsid Accession Nos. | | |
|---|---|---|
| Virus and Serotype | Genome Accession No. | Capsid/VP1 Accession No. |
| AAV1 | NC_002077.1 | NP_049542.1 |
| AAV2 | NC_001401.2 | YP_680426.1 |
| AAV3A | NC_001729.1 | NP_043941.1 |
| AAV3B | NC_001863.1 | NP_045760.1 |
| AAV4 | NC_001829.1 | NP_044927.1 |
| AAV5 | NC_006152.1 | YP_068409.1 |
| AAV6 | NC_001862.1 | NP_045758.1 |
| AAV7 | AF513851.1 | AAN03855.1 |

TABLE 2-continued

| Exemplary AAV Genome and Capsid Accession Nos. | | |
|---|---|---|
| Virus and Serotype | Genome Accession No. | Capsid/VP1 Accession No. |
| AAV8 | AF513852.1 | AAN03857.1 |
| AAV9 | AY530579.1 | AAS99264.1 |
| AAV10 | AY631965.1* | AAT46337.1 |
| AAV11 | AY631966.1* | AAT46339.1 |
| AAV13 | EU285562.1 | ABZ10812.1 |

*Incomplete sequence

TABLE 3

| Amino acid positions of mutations to graft the Gal binding footprint of AAV9 into different AAV strains | | |
|---|---|---|
| AAV Strain | Accession No. | Mutations to Graft Galactose Binding Footprint |
| AAV1 | NP_049542.1 | A267S, SRGSPAGMSVQPK (SEQ ID NO: 25) 464-476SVAGPSNMAVQGR (SEQ ID NO: 6), NFTW (SEQ ID NO: 26) 500-503EFAW (SEQ ID NO: 7) |
| AAV2 | YP_680426.1 | A266S, SQAGASDIRDQSR (SEQ ID NO: 1) 463-475SVAGPSNMAVQGR (SEQ ID NO: 6), EYSW (SEQ ID NO: 3) 499-502EFAW (SEQ ID NO: 7) |
| AAV3a | NP_043941.1 | A266S, SQAGPQSMSLQAR (SEQ ID NO: 27) 464-476SVAGPSNMAVQGR (SEQ ID NO: 6), NFPW (SEQ ID NO: 28) 500-503EFAW (SEQ ID NO: 7) |
| AAV3b | NP_045760.1 | A2665, SQAGPQSMSLQAR (SEQ ID NO: 27) 464-476SVAGPSNMAVQGR (SEQ ID NO: 6), NFPW (SEQ ID NO: 28) 500-503EFAW (SEQ ID NO: 7) |
| AAV4 | NP_044927.1 | insert SSND (SEQ ID NO: 29) before N261, TKLRPTNFSNFKK (SEQ ID NO: 30) 458-470SVAGPSNMAVQGR (SEQ ID NO: 6), DSLI (SEQ ID NO: 31) 499-502EFAW (SEQ ID NO: 7) |
| AAV5 | YP_068409.1 | G257S, NKNLAGRYANTYK (SEQ ID NO: 32) 450-463SVAGPSNMAVQGR (SEQ ID NO: 6), VSAF (SEQ ID NO: 33) 486-489EFAW (SEQ ID NO: 7) |
| AAV6 | NP_045758.1 | A267S, SRGSPAGMSVQPK (SEQ ID NO: 25) 464-476SVAGPSNMAVQGR (SEQ ID NO: 6), NFTW (SEQ ID NO: 26) 500-503EFAW (SEQ ID NO: 7) |
| AAV7 | AAN03855.1 | VQGGPSTMAEQAK (SEQ ID NO: 34) 466-478SVAGPSNMAVQGR (SEQ ID NO: 6), NFAW (SEQ ID NO: 35) 502-505EFAW (SEQ ID NO: 7) |
| AAV8 | AAN03857.1 | A269S, SQGGPNTNANQAK (SEQ ID NO: 36) 466-478SVAGPSNMAVQGR (SEQ ID NO: 6), NFAW (SEQ ID NO: 35) 502-505EFAW (SEQ ID NO: 7) |
| AAV9 | AAS99264.1 | DONOR STRAIN |
| AAV10 | AAT46337.1 | T270S, SQAGPANMSAQAK (SEQ ID NO: 37) 466-478SVAGPSNMAVQGR (SEQ ID NO: 6), N502E |
| Avian AAV | NP_852781.1 | D273S, N275D, insert ANS before D273, SRATKTNMAAQYR (SEQ ID NO: 38) 467-479SVAGPSNMAVQGR (SEQ ID NO: 6), FSVW (SEQ ID NO: 39) 505-508EFAW (SEQ ID NO: 7) |
| BB1 | AAO88209.1 | T270S, SQAGPNNMSAQAR (SEQ ID NO: 40) 466-478SVAGPSNMAVQGR (SEQ ID NO: 6), N502E |
| BB2 | AAO88208.1 | T270S, SQAGPNNMSAQAR (SEQ ID NO: 40) 466-478SVAGPSNMAVQGR (SEQ ID NO: 6), N502E |
| CH5 | AAO88207.1 | AT266-267SS, SQAGPSSMAQQAK (SEQ ID NO: 41) 463-475SVAGPSNMAVQGR (SEQ ID NO: 6) |
| CY2 | AAO88206.1 | T269S, YQGGPSTMAEQAK (SEQ ID NO: 42) 466-478SVAGPSNMAVQGR (SEQ ID NO: 6), N502E |
| CY3 | AAO88205.1 | AT262-263SS, HQAGPNTMAEQSK (SEQ ID NO: 43) 457-469SVAGPSNMAVQGR (SEQ ID NO: 6), N493E |
| CY4 | AAO88204.1 | AT262-263SS, HQAGPNTVAEQSK (SEQ ID NO: 44) 457-469SVAGPSNMAVQGR (SEQ ID NO: 6), N493E |
| CY5 | AAO88203.1 | AT262-263SS, HQAGPNTMAEQSK (SEQ ID NO: 43) 457-469SVAGPSNMAVQGR (SEQ ID NO: 6), N493E |
| CY6 | AAO88202.1 | AT262-263SS, HQAGPNTMAEQSK (SEQ ID NO: 43) 457-469SVAGPSNMAVQGR (SEQ ID NO: 6), N493E |

TABLE 3-continued

Amino acid positions of mutations to graft the Gal
binding footprint of AAV9 into different AAV strains

| AAV Strain | Accession No. | Mutations to Graft Galactose Binding Footprint |
|---|---|---|
| Hu LG15 | AAU05371.1 | A266S, QAGASDIRDQWR (SEQ ID NO: 45) 464-475VAGPSNMAVGQR (SEQ ID NO: 46), DYS499-501EFA |
| Hu S17 | AAU05370.1 | A266S, QAGPTSMSLQAK (SEQ ID NO: 47) 464-475VAGPSNMAVGQR (SEQ ID NO: 46), NFP499-501EFA |
| Hu T17 | AAU05358.1 | A266S, QAGASDIRDQWR (SEQ ID NO: 45) 464-475VAGPSNMAVGQR (SEQ ID NO: 46), DYS499-501EFA |
| Hu T41 | AAU05372.1 | A266S, QAGASDIRDQWR (SEQ ID NO: 45) 464-475VAGPSNMAVGQR (SEQ ID NO: 46), DYS499-501EFA |
| Hu T70 | AAU05364.1 | A266S, QAGASDIRDQWR (SEQ ID NO: 45) 464-475VAGPSNMAVGQR (SEQ ID NO: 46), EYS499-501EFA |
| Hu T71 | AAU05366.1 | A266S, QAGASDIRDQWR (SEQ ID NO: 45) 464-475VAGPSNMAVGQR (SEQ ID NO: 46), DYS499-501EFA |
| Hu T88 | AAU05368.1 | A266S, QAGASDIRDQWR (SEQ ID NO: 45) 464-475VAGPSNMAVGQR (SEQ ID NO: 46), DYS499-501EFA |
| Hu1 | AAS99260.1 | A266S, QAGPTSMSLQAK (SEQ ID NO: 47) 464-475VAGPSNMAVGQR (SEQ ID NO: 46), NFP499-501EFA |
| Hu2 | AAS99270.1 | A266S, QAGPTSMSLQAK (SEQ ID NO: 47) 464-475VAGPSNMAVGQR (SEQ ID NO: 46), NFP499-501EFA |
| Hu3 | AAS99280.1 | AC267-268SS, QAGPTNMSLQAK (SEQ ID NO: 48) 465-476VAGPSNMAVQGR (SEQ ID NO: 49), NFP500-502EFA |
| Hu4 | AAS99287.1 | A266S, QAGPTNMSLQAK (SEQ ID NO: 48) 464-475VAGPSNMAVQGR (SEQ ID NO: 49), NFP499-501EFA |
| Hu6 | AAS99306.1 | T270S, SQAGPNNMSAQAK (SEQ ID NO: 50) 466-478SVAGPSNMAVQGR (SEQ ID NO: 6), N502E |
| Hu7 | AAS99313.1 | A266S, SQAGPTSMSLQAK (SEQ ID NO: 47) 463-475SVAGPSNMAVQGR (SEQ ID NO: 6), NFP499-501EFA |
| Hu9 | AAS99314.1 | A266S, SQAGPTSMSLQAK (SEQ ID NO: 47) 463-475SVAGPSNMAVQGR (SEQ ID NO: 6), NFP499-501EFA |
| Hu10 | AAS99261.1 | A266S, QAGPTSMSLQAK (SEQ ID NO: 47) 464-475VAGPSNMAVGQR (SEQ ID NO: 46), NFP499-501EFA |
| Hu11 | AAS99262.1 | A266S, QAGPTSMSLQAK (SEQ ID NO: 47) 464-475VAGPSNMAVGQR (SEQ ID NO: 46), NFP499-501EFA |
| Hu13 | AAS99263.1 | A266S, QAGASDIRDQSR (SEQ ID NO: 51) 464-475VAGPSNMAVGQRN (SEQ ID NO: 52), EY5499-501EFA |
| Hu15 | AAS99265.1 | A266S, QAGPTSMSLQAK (SEQ ID NO: 47) 464-475VAGPSNMAVGQR (SEQ ID NO: 46), NFP499-501EFA |
| Hu16 | AAS99266.1 | A266S, QAGPTSMSLQAK (SEQ ID NO: 47) 464-475VAGPSNMAVGQR (SEQ ID NO: 46), NFP499-501EFA |
| Hu17 | AAS99267.1 | T270S, QAGPNNMSAQAK (SEQ ID NO: 53) 467-478VAGPSNMAVGQR (SEQ ID NO: 46), NFA502-504EFA |
| Hu18 | AAS99268.1 | A266S, QAGPTSMSLQAK (SEQ ID NO: 47) 464-475VAGPSNMAVGQR (SEQ ID NO: 46), NFP499-501EFA |
| Hu19 | AAS99269.1 | A266S, QAGASDIRDQSR (SEQ ID NO: 51) 464-475VAGPSNMAVGQRN (SEQ ID NO: 52), DYS499-501EFA |
| Hu20 | AAS99271.1 | A266S, QAGASDIRDQSR (SEQ ID NO: 51) 464-475VAGPSNMAVGQRN (SEQ ID NO: 52), DYS499-501EFA |
| Hu21 | AAS99272.1 | A266S, QAGASDIRDQSR (SEQ ID NO: 51) 464-475VAGPSNMAVGQRN (SEQ ID NO: 52), DYS499-501EFA |
| Hu22 | AAS99273.1 | A266S, QAGASDIRDQSR (SEQ ID NO: 51) 464-475VAGPSNMAVGQRN (SEQ ID NO: 52), DYS499-501EFA |

TABLE 3-continued

Amino acid positions of mutations to graft the Gal binding footprint of AAV9 into different AAV strains

| AAV Strain | Accession No. | Mutations to Graft Galactose Binding Footprint |
|---|---|---|
| Hu23 | AAS99274.1 | A266S, QAGASDIRDQSR (SEQ ID NO: 51) 464-475VAGPSNMAVGQRN (SEQ ID NO: 52), DYS499-501EFA |
| Hu24 | AAS99275.1 | A266S, QAGASDIRDQSR (SEQ ID NO: 51) 464-475VAGPSNMAVGQRN (SEQ ID NO: 52), DYS499-501EFA |
| Hu25 | AAS99276.1 | A266S, QAGPTSMSLQAK (SEQ ID NO: 47) 464-475VAGPSNMAVGQR (SEQ ID NO: 46), NFP499-501EFA |
| Hu27 | AAS99277.1 | A266S, QAGASDVRDQSR (SEQ ID NO: 54) 464-475VAGPSNMAVGQR (SEQ ID NO: 46), DYS499-501EFA |
| Hu28 | AAS99278.1 | A266S, QAGASDIQDQSR (SEQ ID NO: 55) 464-475VAGPSNMAVGQR (SEQ ID NO: 46), EYS499-501EFA |
| Hu29 | AAS99279.1 | A266S, QAGASDIRDQSR (SEQ ID NO: 51) 464-475VAGPSNMAVGQRN (SEQ ID NO: 52), EYS499-501EFA |
| Hu34 | AAS99283.1 | A266S, QAGASDIRDQSR (SEQ ID NO: 51) 464-475VAGPSNMAVQGR (SEQ ID NO: 49), YS500-502FA |
| Hu35 | AAS99284.1 | A266S, QAGASDIRDQSR (SEQ ID NO: 51) 464-475VAGPSNMAVQGR (SEQ ID NO: 49), YS500-502FA |
| Hu37 | AAS99285.1 | T270S, QAGPANMSAQAK (SEQ ID NO: 56) 467-478VAGPSNMAVQGR (SEQ ID NO: 49), N502E |
| Hu39 | AAS99286.1 | T270S, RAGPSNMSAQAR (SEQ ID NO: 57) 467-478VAGPSNMAVQGR (SEQ ID NO: 49), N502E |
| Hu40 | AAS99288.1 | T270S, QAGPANMSAQAK (SEQ ID NO: 56) 467-478VAGPSNMAVQGR (SEQ ID NO: 49), N502E |
| Hu41 | AAS99289.1 | T270S, QAGPANMSAQAK (SEQ ID NO: 56) 467-478VAGPSNMAVQGR (SEQ ID NO: 49), N502E |
| Hu42 | AAS99290.1 | T270S, QAGPANMSAQAK (SEQ ID NO: 56) 467-478VAGPSNMAVQGR (SEQ ID NO: 49), N502E |
| Hu43 | AAS99291.1 | A268S, RGSPAGMSVQPK (SEQ ID NO: 58) 466-477VAGPSNMAVQGR (SEQ ID NO: 49), NFT502-503EFA |
| Hu44 | AAS99292.1 | A267S, RGSPAGMSVQPK (SEQ ID NO: 58) 465-476VAGPSNMAVQGR (SEQ ID NO: 49), NFT500-502EFA |
| Hu45 | AAS99293.1 | A266S, QAGASDIRDQSR (SEQ ID NO: 51) 464-475VAGPSNMAVQGR (SEQ ID NO: 49), YS500-502FA |
| Hu46 | AAS99294.1 | A267S, RGSPAGMSVQPK (SEQ ID NO: 58) 465-476VAGPSNMAVQGR (SEQ ID NO: 49), NFT500-502EFA |
| Hu47 | AAS99295.1 | A266S, S270N, QAGASDIRDQSR (SEQ ID NO: 51) 464-475VAGPSNMAVQGR (SEQ ID NO: 49), YS500-502FA |
| Hu48 | AAS99296.1 | A267S, RGSPAGMSVQPK (SEQ ID NO: 58) 465-476VAGPSNMAVQGR (SEQ ID NO: 49), NFT500-502EFA |
| Hu49 | AAS99297.1 | A266S, QAGASDIRDQSR (SEQ ID NO: 51) 464-475VAGPSNMAVQGR (SEQ ID NO: 49), YS500-502FA |
| Hu51 | AAS99298.1 | A266S, QAGASDIRDQSR (SEQ ID NO: 51) 464-475VAGPSNMAVQGR (SEQ ID NO: 49), YS500-502FA |
| Hu52 | AAS99299.1 | A266S, QAGASDIRDQSR (SEQ ID NO: 51) 464-475VAGPSNMAVQGR (SEQ ID NO: 49), YS500-502FA |
| Hu54 | AAS99301.1 | A266S, QAGPTNMSLQAK (SEQ ID NO: 48) 463-474VAGPSNMAVQGR (SEQ ID NO: 49), NFP498-500EFA |
| Hu55 | AAS99302.1 | A266S, QAGPTNMSLQAK (SEQ ID NO: 48) 463-474VAGPSNMAVQGR (SEQ ID NO: 49), NFP498-500EFA |
| Hu56 | AAS99303.1 | A266S, QAGASDIRDQSR (SEQ ID NO: 51) 464-475VAGPSNMAVQGR (SEQ ID NO: 49), YS500-502FA |
| Hu57 | AAS99304.1 | A265S, QAGASDIRDQSR (SEQ ID NO: 51) 463-474VAGPSNMAVQGR (SEQ ID NO: 49), YS499-500FA |

TABLE 3-continued

Amino acid positions of mutations to graft the Gal binding footprint of AAV9 into different AAV strains

| AAV Strain | Accession No. | Mutations to Graft Galactose Binding Footprint |
|---|---|---|
| Hu58 | AAS99305.1 | A266S, QAGASDIRDQSR (SEQ ID NO: 51) 464-475VAGPSNMAVQGR (SEQ ID NO: 49), YS500-502FA |
| Hu60 | AAS99307.1 | A266S, SQAGPTMNSLQAK (SEQ ID NO: 59) 463-475SVAGPSNMAVQGR (SEQ ID NO: 6), NFP499-501EFA |
| Hu61 | AAS99308.1 | A266S, SQAGPTMNSLQAK (SEQ ID NO: 59) 463-475SVAGPSNMAVQGR (SEQ ID NO: 6), NFP499-501EFA |
| Hu63 | AAS99309.1 | A266S, SQAGASDIRDQSR (SEQ ID NO: 1) 463-475SVAGPSNMAVQGR (SEQ ID NO: 6), YS500-501FA |
| Hu64 | AAS99310.1 | A266S, SQAGASDIRDQSR (SEQ ID NO: 1) 463-475SVAGPSNMAVQGR (SEQ ID NO: 6), YS500-501FA |
| Hu66 | AAS99311.1 | T270S, SQAGPANMSAQAK (SEQ ID NO: 37) 466-478SVAGPSNMAVQGR (SEQ ID NO: 6), N502E |
| Hu67 | AAS99312.1 | T270S, SQAGPANMSAQAK (SEQ ID NO: 37) 466-478SVAGPSNMAVQGR (SEQ ID NO: 6), N502E |
| Rh1 | AAS99241.1 | T270S, SQAGPSSMANQAR (SEQ ID NO: 60) 465-477SVAGPSNMAVQGR (SEQ ID NO: 6), N501E |
| Rh2 | AAO88193.1 | T270S, SQAGPANMSAQAK (SEQ ID NO: 37) 466-478SVAGPSNMAVQGR (SEQ ID NO: 6), N502E |
| Rh8 | AAO88183.1 | T270S, SQAGPSSMANQAR (SEQ ID NO: 60) 464-476SVAGPSNMAVQGR (SEQ ID NO: 6), N500E |
| Rh10 | AAO88201.1 | T270S, SQAGPNNMSAQAK (SEQ ID NO: 50) 466-478SVAGPSNMAVQGR (SEQ ID NO: 6), N502E |
| Rh12 | AAO88200.1 | T265S, SQAGPNNMSAQAK (SEQ ID NO: 50) 461-473SVAGPSNMAVQGR (SEQ ID NO: 6), N497E |
| Rh13 | AAO88199.1 | AT262-263SS, HQAGPNTMAEQSK (SEQ ID NO: 43) 457-469SVAGPSNMAVQGR (SEQ ID NO: 6), N493E |
| Rh14 | AAO88198.1 | T265S, SQAGPNNMSAQAK (SEQ ID NO: 50) 461-473SVAGPSNMAVQGR (SEQ ID NO: 6), N497E |
| Rh16 | AAO88197.1 | AT262-263SS, SQAGPNNMSAQAK (SEQ ID NO: 50) 459-471SVAGPSNMAVQGR (SEQ ID NO: 6), N495E |
| Rh17 | AAO88196.1 | AT262-263SS, SQAGPNNMSAQAK (SEQ ID NO: 50) 459-471SVAGPSNMAVQGR (SEQ ID NO: 6), N495E |
| Rh18 | AAO88195.1 | T270S, SQAGPNNMSAQAK (SEQ ID NO: 50) 466-478SVAGPSNMAVQGR (SEQ ID NO: 6), N502E |
| Rh19 | AAO88194.1 | T270S, HQAGPNTMAEQSK (SEQ ID NO: 43) 464-476SVAGPSNMAVQGR (SEQ ID NO: 6), N500E |
| Rh22 | AAO88192.1 | AT262-263SS, HQAGPNTMAEQSK (SEQ ID NO: 43) 457-469SVAGPSNMAVQGR (SEQ ID NO: 6), N493E |
| Rh23 | AAO88191.1 | T270S, HQAGPNTMAEQSK (SEQ ID NO: 43) 464-476SVAGPSNMAVQGR (SEQ ID NO: 6), N500E |
| Rh24 | AAO88190.1 | T265S, SQAGPNNMSAQAK (SEQ ID NO: 50) 461-473SVAGPSNMAVQGR (SEQ ID NO: 6), N497E |
| Rh25 | AAS99242.1 | T270S, SQAGPNNMSAQAK (SEQ ID NO: 50) 466-478SVAGPSNMAVQGR (SEQ ID NO: 6), N502E |
| Rh26 | AAO89501.1 | T188S, YQGGPTTMAEQAK (SEQ ID NO: 61) 385-397SVAGPSNMAVQGR (SEQ ID NO: 6), N421E |
| Rh27 | AAO89502.1 | T188S, YQGGPTTMAEQAK (SEQ ID NO: 61) 385-397SVAGPSNMAVQGR (SEQ ID NO: 6), N421E |
| Rh31 | AAO89500.1 | T188S, YQGGPTTMAEQAK (SEQ ID NO: 61) 385-397SVAGPSNMAVQGR (SEQ ID NO: 6), N421E |
| Rh32 | AAO88189.1 | insert SGGSS before N259, GKIRSGDFAFYRK (SEQ ID NO: 62) 457-469SVAGPSNMAVQGR (SEQ ID NO: 6), NALL498-501EFAW (SEQ ID NO: 7) |
| Rh33 | AAO88188.1 | insert SGGSS before N259, GKIRSGDFAFYRK (SEQ ID NO: 62) 457-469SVAGPSNMAVQGR (SEQ ID NO: 6), NALL498-501EFAW (SEQ ID NO: 7) |
| Rh34 | AAO88187.1 | insert SGGSS before N259, GKIRSGDFAFYRK (SEQ ID NO: 62) 457-469SVAGPSNMAVQGR (SEQ ID NO: 6), NALL498-501EFAW (SEQ ID NO: 7) |
| Rh35 | AAO88186.1 | AT263-264SS, HQAGPNTMAEQSK (SEQ ID NO: 43) 458-470SVAGPSNMAVQGR (SEQ ID NO: 6), N494E |
| Rh36 | AAO88185.1 | AT263-264SS, HQAGPNTMAEQSK (SEQ ID NO: 43) 458-470SVAGPSNMAVQGR (SEQ ID NO: 6), N494E |

TABLE 3-continued

Amino acid positions of mutations to graft the Gal binding footprint of AAV9 into different AAV strains

| AAV Strain | Accession No. | Mutations to Graft Galactose Binding Footprint |
|---|---|---|
| Rh37 | AAO88184.1 | AT263-264SS, HQAGPNTMAEQSK (SEQ ID NO: 43) 458-470SVAGPSNMAVQGR (SEQ ID NO: 6), N494E |
| Rh38 | AAS99243.1 | T270S, SQAGPANMSAQAK (SEQ ID NO: 37) 466-478SVAGPSNMAVQGR (SEQ ID NO: 6), N502E |
| Rh40 | AAS99244.1 | T270S. SQAGPANMSARAK (SEQ ID NO: 63) 466-478SVAGPSNMAVQGR (SEQ ID NO: 6), N502E |
| Rh43 | AAS99245.1 | AT268-269SS, SQGGPNTMANQAK (SEQ ID NO: 64) 456-477SVAGPSNMAVQGR (SEQ ID NO: 6), N501E |
| Rh48 | AAS99246.1 | T269S, YQGGPTTMAEQAK (SEQ ID NO: 61) 466-478SVAGPSNMAVQGR (SEQ ID NO: 6), N502E |
| Rh49 | AAS99247.1 | T270S, SQAGPSNMSAQAR (SEQ ID NO: 64) 466-478SVAGPSNMAVQGR (SEQ ID NO: 6), N502E |
| Rh50 | AAS99248.1 | T270S, SQAGPSNMSAQAR (SEQ ID NO: 64) 466-478SVAGPSNMAVQGR (SEQ ID NO: 6), N502E |
| Rh51 | AAS99249.1 | T270S, SQAGPSNMSAQAR (SEQ ID NO: 64) 466-478SVAGPSNMAVQGR (SEQ ID NO: 6), N502E |
| Rh52 | AAS99250.1 | T270S, SQAGPSNMSAQAR (SEQ ID NO: 64) 466-478SVAGPSNMAVQGR (SEQ ID NO: 6), N502E |
| Rh53 | AAS99251.1 | T270S, SQAGPSNMSAQAR (SEQ ID NO: 64) 466-478SVAGPSNMAVQGR (SEQ ID NO: 6), N502E |
| Rh54 | AAS99252.1 | T269S, YQGGPTTMAEQAK (SEQ ID NO: 61) 466-478SVAGPSNMAVQGR (SEQ ID NO: 6), N502E |
| Rh55 | AAS99253.1 | T269S, YQGGPTTMAEQAK (SEQ ID NO: 61) 466-478SVAGPSNMAVQGR (SEQ ID NO: 6), N502E |
| Rh57 | AAS99254.1 | T270S, SQAGPSNMSAQAR (SEQ ID NO: 64) 466-478SVAGPSNMAVQGR (SEQ ID NO: 6), N502E |
| Rh58 | AAS99255.1 | T270S, SQAGPSNMSAQAR (SEQ ID NO: 64) 466-478SVAGPSNMAVQGR (SEQ ID NO: 6), N502E |
| Rh60 | AAS99256.1 | T270S, SQAGPSNMSAQAR (SEQ ID NO: 64) 466-478SVAGPSNMAVQGR (SEQ ID NO: 6), N502E |
| Rh61 | AAS99257.1 | T270S, SQAGPSNMSAQAR (SEQ ID NO: 64) 466-478SVAGPSNMAVQGR (SEQ ID NO: 6), N502E |
| Rh62 | AAS99258.1 | T269S, YQGGPTTMAEQAK (SEQ ID NO: 61) 466-478SVAGPSNMAVQGR (SEQ ID NO: 6), N502E |
| Rh64 | AAS99259.1 | T270S, SQAGPSNMSAQAR (SEQ ID NO: 64) 466-478SVAGPSNMAVQGR (SEQ ID NO: 6), N502E |

REFERENCES

1. Olofsson, S, Bergstrom, T (2005). Glycoconjugate glycans as viral receptors. *Ann Med* 37: 154-172.
2. Neu, U, Bauer, J, Stehle, T (2011). Viruses and sialic acids: rules of engagement. *Curr Opin Struct Biol* 21: 610-618.
3. Agbandje-McKenna, M, Kleinschmidt, J (2011). AAV capsid structure and cell interactions. *Methods Mol Biol* 807: 47-92.
4. Asokan, A, Schaffer, D V, Jude Samulski, R (2012). The AAV Vector Toolkit: Poised at the Clinical Crossroads. *Mol Ther* 20: 699-708.
5. Halbert, C L, Allen, J M, Miller, A D (2001). Adeno-associated virus type 6 (AAV6) vectors mediate efficient transduction of airway epithelial cells in mouse lungs compared to that of AAV2 vectors. *J Virol* 75: 6615-6624.
6. Wu, Z, Asokan, A, Grieger, J C, Govindasamy, L, Agbandje-McKenna, M, Samulski, R J (2006). Single amino acid changes can influence titer, heparin binding, and tissue tropism in different adeno-associated virus serotypes. *J Virol* 80: 11393-11397.
7. Ng, R, Govindasamy, L, Gurda, B L, McKenna, R, Kozyreva, O G, Samulski, R J, Parent, K N, Baker, T S, Agbandje-McKenna, M (2010). Structural characterization of the dual glycan binding adeno-associated virus serotype 6. *J Virol* 84: 12945-12957.
8. Xie, Q, Lerch, T F, Meyer, N L, Chapman, M S (2011). Structure-function analysis of receptor-binding in adeno-associated virus serotype 6 (AAV-6). *Virology* 420: 10-19.
9. Lerch, T F, Chapman, M S (2012). Identification of the heparin binding site on adeno-associated virus serotype 3B (AAV-3B). *Virology* 423: 6-13.
10. Opie, S R, Warrington, K H, Jr, Agbandje-McKenna, M, Zolotukhin, S, Muzyczka, N (2003). Identification of amino acid residues in the capsid proteins of adeno-associated virus type 2 that contribute to heparan sulfate proteoglycan binding. *J Virol* 77: 6995-7006.
11. Levy, H C, Bowman, V D, Govindasamy, L, McKenna, R, Nash, K, Warrington, K, Chen, W, Muzyczka, N, Yan, X, Baker, T S, Agbandje-McKenna, M (2009). Heparin binding induces conformational changes in Adeno-associated virus serotype 2. *J Struct Biol* 165: 146-156.
12. O'Donnell, J, Taylor, K A, Chapman, M S (2009). Adeno-associated virus-2 and its primary cellular receptor—Cryo-EM structure of a heparin complex. *Virology* 385: 434-443.
13. Bell, C L, Gurda, B L, Van Vliet, K, Agbandje-McKenna, M, Wilson, J M (2012). Identification of the galactose binding domain of the AAV9 capsid. *J Virol*
14. Grieger, J C, Choi, V W, Samulski, R J (2006). Production and characterization of adeno-associated viral vectors. *Nat Protoc* 1: 1412-1428.
15. Asokan, A, Conway, J C, Phillips, J L, Li, C, Hegge, J, Sinnott, R, Yadav, S, DiPrimio, N, Nam, H J, Agbandje- McKenna, M, McPhee, S, Wolff, J, Samulski, R J (2010). Reengineering a receptor footprint of adeno-associated virus enables selective and systemic gene transfer to muscle. *Nat Biotechnol* 28: 79-82.
16. Summerford, C, Samulski, R J (1998). Membrane-associated heparan sulfate proteoglycan is a receptor for adeno-associated virus type 2 virions. *J Virol* 72: 1438-1445.
17. Bell, C L, Vandenberghe, L H, Bell, P, Limberis, M P, Gao, G P, Van Vliet, K, Agbandje-McKenna, M, Wilson, J M (2011). The AAV9 receptor and its modification to improve in vivo lung gene transfer in mice. *J Clin Invest* 121: 2427-2435.
18. Shen, S, Bryant, K D, Brown, S M, Randell, S H, Asokan, A (2011). Terminal N-linked galactose is the primary receptor for adeno-associated virus 9. *J Biol Chem* 286: 13532-13540.
19. Gao, G P, Alvira, M R, Wang, L, Calcedo, R, Johnston, J, Wilson, J M (2002). Novel adeno-associated viruses from rhesus monkeys as vectors for human gene therapy. *Proc Natl Acad Sci USA* 99: 11854-11859.
20. Inagaki, K, Fuess, S, Storm, T A, Gibson, G A, Mctiernan, C F, Kay, M A, Nakai, H (2006). Robust systemic transduction with AAV9 vectors in mice: efficient global cardiac gene transfer superior to that of AAV8. *Mol Ther* 14: 45-53.
21. Zincarelli, C, Soltys, S, Rengo, G, Rabinowitz, J E (2008). Analysis of AAV serotypes 1-9 mediated gene expression and tropism in mice after systemic injection. *Mol Ther* 16: 1073-1080.
22. Wang, J, Xie, J, Lu, H, Chen, L, Hauck, B, Samulski, R J, Xiao, W (2007). Existence of transient functional double-stranded DNA intermediates during recombinant AAV transduction. *Proc Natl Acad Sci USA* 104: 13104-13109.
23. Wang, L, Bell, P, Lin, J, Calcedo, R, Tarantal, A F, Wilson, J M (2011). AAV8-mediated hepatic gene transfer in infant rhesus monkeys (*Macaca mulatta*). *Mol Ther* 19: 2012-2020.
24. Imai, M, Watanabe, T, Hatta, M, Das, S C, Ozawa, M, Shinya, K, Zhong, G, Hanson, A, Katsura, H, Watanabe, S, Li, C, Kawakami, E, Yamada, S, Kiso, M, Suzuki, Y, Maher, E A, Neumann, G, Kawaoka, Y (2012). Experimental adaptation of an influenza H5 HA confers respiratory droplet transmission to a reassortant H5 HA/H1N1 virus in ferrets. *Nature* 486: 420-428.
25. Herfst, S, Schrauwen, E J, Linster, M, Chutinimitkul, S, de Wit, E, Munster, V J, Sorrell, E M, Bestebroer, T M, Burke, D F, Smith, D J, Rimmelzwaan, G F, Osterhaus, A D, Fouchier, R A (2012). Airborne transmission of influenza A/H5N1 virus between ferrets. *Science* 336: 1534-1541.
26. High, K A (2012). The gene therapy journey for hemophilia: are we there yet? *Blood*
27. Mingozzi, F, High, K A (2011). Therapeutic in vivo gene transfer for genetic disease using AAV: progress and challenges. *Nat Rev Genet* 12: 341-355.
28. McCarty, D M (2008). Self-complementary AAV vectors; advances and applications. *Mol Ther* 16: 1648-1656.
29. Zhong, L, Li, B, Mah, C S, Govindasamy, L, Agbandje-McKenna, M, Cooper, M, Herzog, R W, Zolotukhin, I, Warrington, K H, Jr, Weigel-Van Aken, K A, Hobbs, J A, Zolotukhin, S, Muzyczka, N, Srivastava, A (2008). Next generation of adeno-associated virus 2 vectors: point mutations in tyrosines lead to high-efficiency transduction at lower doses. *Proc Natl Acad Sci USA* 105: 7827-7832.
30. Xie, Q, Bu, W, Bhatia, S, Hare, J, Somasundaram, T, Azzi, A, Chapman, M S (2002). The atomic structure of adeno-associated virus (AAV-2), a vector for human gene therapy. *Proc Natl Acad Sci USA* 99: 10405-10410.
31. DiMattia, M A, Nam, H J, Van Vliet, K, Mitchell, M, Bennett, A, Gurda, B L, McKenna, R, Olson, N H, Sinkovits, R S, Potter, M, Byrne, B J, Aslanidi, G, Zolotukhin, S, Muzyczka, N, Baker, T S, Agbandje-McKenna, M (2012). Structural insight into the unique properties of adeno-associated virus serotype 9. *J Virol* 86: 6947-6958.
32. Arnold, K, Bordoli, L, Kopp, J, Schwede, T (2006). The SWISS-MODEL workspace: a web-based environment for protein structure homology modelling. *Bioinformatics* 22: 195-201.
33. Carrillo-Tripp, M, Shepherd, C M, Borelli, I A, Venkataraman, S, Lander, G, Natarajan, P, Johnson, J E, Brooks, C L, 3rd, Reddy, V S (2009). VIPERdb2: an enhanced and web API enabled relational database for structural virology. *Nucleic Acids Res* 37: D436-42.
34. Kern, A, Schmidt, K, Leder, C, Muller, O J, Wobus, C E, Bettinger, K, Von der Lieth, C W, King, J A, Kleinschmidt, J A (2003). Identification of a heparin-binding motif on adeno-associated virus type 2 capsids. *J Virol* 77: 11072-11081.

That which is claimed is:

1. An adeno-associated virus 2 (AAV2) capsid protein comprising an AAV2 capsid amino acid sequence into which the following substitutions have been introduced, based on the amino acid sequence of SEQ ID NO:65: A266S, Q464V, A467P, D469N, I470M, R471A, D472V, S474G, Y500F and S501A (AAV2 VP1 numbering).

2. An adeno-associated virus 2 (AAV2) capsid protein comprising an AAV2 capsid amino acid sequence into which the following substitutions have been introduced, based on the amino acid sequence of SEQ ID NO:65: A266S, Q464V, A467P, D469N, I470M, R471A, D472V, S474G, Y500F and S501A, and wherein amino acids 585-590 are substituted with QQNTAP (AAV2 VP1 numbering).

3. An adeno-associated virus 8 (AAV8) capsid protein comprising an AAV8 capsid amino acid sequence into which the following substitutions have been introduced, based on the amino acid sequence of SEQ ID NO:66: A269S, Q467V, N471S, N475V, A477G, K478R, N502E (AAV8 VP1 numbering).

4. An AAV capsid comprising the AAV capsid protein of claim 1.

5. A virus vector comprising:
   (a) the AAV capsid of claim 4; and
   (b) a nucleic acid comprising at least one terminal repeat sequence, wherein the nucleic acid is encapsidated by the AAV capsid.

6. A composition comprising the virus vector of claim 5 in a pharmaceutically acceptable carrier.

7. A method of introducing a nucleic acid into a cell, comprising contacting the cell with the virus vector of claim 5.

8. The method of claim 7, wherein the cell is in a subject.

9. The method of claim 8, wherein the subject is a human subject.

10. An AAV capsid comprising the AAV capsid protein of claim 2.

11. A virus vector comprising:
   (a) the AAV capsid of claim 10; and
   (b) a nucleic acid comprising at least one terminal repeat sequence, wherein the nucleic acid is encapsidated by the AAV capsid.

12. A composition comprising the virus vector of claim 11 in a pharmaceutically acceptable carrier.

13. A method of introducing a nucleic acid into a cell, comprising contacting the cell with the virus vector of claim 11.

14. The method of claim 13, wherein the cell is in a subject.

15. The method of claim 14, wherein the subject is a human subject.

16. An AAV capsid comprising the AAV capsid protein of claim 3.

17. A virus vector comprising:
   (a) the AAV capsid of claim 16; and
   (b) a nucleic acid comprising at least one terminal repeat sequence, wherein the nucleic acid is encapsidated by the AAV capsid.

18. A composition comprising the virus vector of claim 17 in a pharmaceutically acceptable carrier.

19. A method of introducing a nucleic acid into a cell, comprising contacting the cell with the virus vector of claim 17.

20. The method of claim 19, wherein the cell is in a subject.

21. The method of claim 20, wherein the subject is a human subject.

* * * * *

UNITED STATES PATENT AND TRADEMARK OFFICE
CERTIFICATE OF CORRECTION

PATENT NO. : 10,077,291 B2
APPLICATION NO. : 14/777070
DATED : September 18, 2018
INVENTOR(S) : Asokan et al.

It is certified that error appears in the above-identified patent and that said Letters Patent is hereby corrected as shown below:

On the Title Page

Item (56) References Cited, Other Publications, 2nd Gao et al. cite:
Please correct "Glades" to read -- Clades --

In the Specification

Column 3, Line 59: Please correct "mean s.e.m." to read -- mean ± s.e.m. --

Column 14, Line 61: Please correct "interferon-α" to read -- interferon-γ --

Column 31, Line 19: Please correct "·D472V" to read -- D472V --

Signed and Sealed this
Eleventh Day of December, 2018

Andrei Iancu
*Director of the United States Patent and Trademark Office*

SEQUENCE LISTING

```
<160> NUMBER OF SEQ ID NOS: 66

<210> SEQ ID NO 1
<211> LENGTH: 13
<212> TYPE: PRT
<213> ORGANISM: adeno-associated virus 2

<400> SEQUENCE: 1

Ser Gln Ala Gly Ala Ser Asp Ile Arg Asp Gln Ser Arg
1               5                   10

<210> SEQ ID NO 2
<211> LENGTH: 13
<212> TYPE: PRT
<213> ORGANISM: Artificial
<220> FEATURE:
<223> OTHER INFORMATION: AAV amino acid substitution sequence
```

```
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 2

Ser Xaa Ala Gly Xaa Ser Xaa Xaa Xaa Xaa Gln Xaa Arg
1               5                   10

<210> SEQ ID NO 3
<211> LENGTH: 4
<212> TYPE: PRT
<213> ORGANISM: adeno-associated virus 2

<400> SEQUENCE: 3

Glu Tyr Ser Trp
1

<210> SEQ ID NO 4
<211> LENGTH: 4
<212> TYPE: PRT
<213> ORGANISM: Artificial
<220> FEATURE:
<223> OTHER INFORMATION: AAV amino acid substitution sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 4

Glu Xaa Xaa Trp
1

<210> SEQ ID NO 5
<211> LENGTH: 4
<212> TYPE: PRT
<213> ORGANISM: adeno-associated virus 9

<400> SEQUENCE: 5

Asn Met Ala Val
1

<210> SEQ ID NO 6
<211> LENGTH: 13
<212> TYPE: PRT
<213> ORGANISM: adeno-associated virus 9

<400> SEQUENCE: 6

Ser Val Ala Gly Pro Ser Asn Met Ala Val Gln Gly Arg
1               5                   10

<210> SEQ ID NO 7
<211> LENGTH: 4
<212> TYPE: PRT
<213> ORGANISM: adeno-associated virus 9
```

<400> SEQUENCE: 7

Glu Phe Ala Trp
1

<210> SEQ ID NO 8
<211> LENGTH: 13
<212> TYPE: PRT
<213> ORGANISM: Artificial
<220> FEATURE:
<223> OTHER INFORMATION: AAV amino acid substitution sequence
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid

<400> SEQUENCE: 8

Ser Xaa Xaa Xaa Pro Xaa Xaa Met Xaa Val Gln Xaa Xaa
1               5                   10

<210> SEQ ID NO 9
<211> LENGTH: 4
<212> TYPE: PRT
<213> ORGANISM: Artificial
<220> FEATURE:
<223> OTHER INFORMATION: AAV amino acid substitution sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 9

Xaa Phe Xaa Trp
1

<210> SEQ ID NO 10
<211> LENGTH: 13
<212> TYPE: PRT
<213> ORGANISM: Artificial
<220> FEATURE:
<223> OTHER INFORMATION: AAV amino acid substitution sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 10

Ser Xaa Ala Gly Pro Xaa Xaa Met Xaa Xaa Gln Xaa Arg
1               5                   10

<210> SEQ ID NO 11
<211> LENGTH: 13
<212> TYPE: PRT
<213> ORGANISM: Artificial
<220> FEATURE:
<223> OTHER INFORMATION: AAV amino acid substitution sequence
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(13)
<223> OTHER INFORMATION: Xaa can be any naturally occurring amino acid

<400> SEQUENCE: 11

Xaa Xaa Xaa Xaa Pro Xaa Asn Xaa Xaa Xaa Xaa Xaa Xaa
1               5                   10

<210> SEQ ID NO 12
<211> LENGTH: 4
<212> TYPE: PRT
<213> ORGANISM: Artificial
<220> FEATURE:
<223> OTHER INFORMATION: AAV amino acid substitution sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 12

Xaa Xaa Xaa Xaa
1

<210> SEQ ID NO 13
<211> LENGTH: 13
<212> TYPE: PRT
<213> ORGANISM: Artificial
<220> FEATURE:
<223> OTHER INFORMATION: AAV amino acid substitution sequence
<220> FEATURE:
<221> NAME/KEY: misc_feature
<222> LOCATION: (1)..(8)
<223> OTHER INFORMATION: Xaa can be any naturally occurring amino acid
<220> FEATURE:
<221> NAME/KEY: misc_feature
<222> LOCATION: (10)..(13)
<223> OTHER INFORMATION: Xaa can be any naturally occurring amino acid

<400> SEQUENCE: 13

Xaa Xaa Xaa Xaa Xaa Xaa Xaa Xaa Ala Xaa Xaa Xaa Xaa
1               5                   10

<210> SEQ ID NO 14
<211> LENGTH: 4
<212> TYPE: PRT
<213> ORGANISM: Artificial
<220> FEATURE:
<223> OTHER INFORMATION: AAV amino acid substitution sequence
<220> FEATURE:
<221> NAME/KEY: misc_feature
<222> LOCATION: (1)..(2)
<223> OTHER INFORMATION: Xaa can be any naturally occurring amino acid

```
<220> FEATURE:
<221> NAME/KEY: misc_feature
<222> LOCATION: (4)..(4)
<223> OTHER INFORMATION: Xaa can be any naturally occurring amino acid

<400> SEQUENCE: 14

Xaa Xaa Ala Xaa
1

<210> SEQ ID NO 15
<211> LENGTH: 13
<212> TYPE: PRT
<213> ORGANISM: Artificial
<220> FEATURE:
<223> OTHER INFORMATION: AAV amino acid substitution sequence
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid

<400> SEQUENCE: 15

Xaa Xaa Xaa Gly Pro Ser Xaa Met Ala Xaa Gln Xaa Xaa
1               5                   10

<210> SEQ ID NO 16
<211> LENGTH: 4
<212> TYPE: PRT
<213> ORGANISM: Artificial
<220> FEATURE:
<223> OTHER INFORMATION: AAV amino acid substitution sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 16

Xaa Phe Ala Trp
1

<210> SEQ ID NO 17
<211> LENGTH: 13
<212> TYPE: PRT
<213> ORGANISM: Artificial
<220> FEATURE:
<223> OTHER INFORMATION: AAV amino acid substitution sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
```

-continued

<400> SEQUENCE: 17

Ser Xaa Xaa Gly Pro Xaa Xaa Met Ala Xaa Gln Xaa Xaa
1               5                   10

<210> SEQ ID NO 18
<211> LENGTH: 13
<212> TYPE: PRT
<213> ORGANISM: Artificial
<220> FEATURE:
<223> OTHER INFORMATION: AAV amino acid substitution sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid

<400> SEQUENCE: 18

Xaa Xaa Ala Gly Pro Xaa Asn Met Xaa Xaa Gln Xaa Xaa
1               5                   10

<210> SEQ ID NO 19
<211> LENGTH: 96
<212> TYPE: DNA
<213> ORGANISM: Artificial
<220> FEATURE:
<223> OTHER INFORMATION: Mutagenesis primer sequence

<400> SEQUENCE: 19
ggaaccacca cgcagtcaag gcttcagttt tctgtggccg gacccagtaa catggctgtc     60
cagggaagga actggcttcc tggaccctgt taccgc                              96

<210> SEQ ID NO 20
<211> LENGTH: 60
<212> TYPE: DNA
<213> ORGANISM: Artificial
<220> FEATURE:
<223> OTHER INFORMATION: Mutagenesis primer sequence

<400> SEQUENCE: 20
gacatctgcg gataacaaca acagtgaatt tgcttggact ggagctacca agtaccacct     60

<210> SEQ ID NO 21
<211> LENGTH: 22
<212> TYPE: DNA
<213> ORGANISM: Artificial
<220> FEATURE:
<223> OTHER INFORMATION: qPCR primer sequence

<400> SEQUENCE: 21
agggcacctc catctcggaa ac                                             22

<210> SEQ ID NO 22
<211> LENGTH: 23
<212> TYPE: DNA
<213> ORGANISM: Artificial
<220> FEATURE:
<223> OTHER INFORMATION: qPCR primer sequence

```
<400> SEQUENCE: 22
ggacccaagg actacctcaa ggg                                          23

<210> SEQ ID NO 23
<211> LENGTH: 24
<212> TYPE: DNA
<213> ORGANISM: Artificial
<220> FEATURE:
<223> OTHER INFORMATION: qPCR primer sequence

<400> SEQUENCE: 23
aaaagcactc tgattgacaa atac                                         24

<210> SEQ ID NO 24
<211> LENGTH: 22
<212> TYPE: DNA
<213> ORGANISM: Artificial
<220> FEATURE:
<223> OTHER INFORMATION: qPCR primer sequence

<400> SEQUENCE: 24
ccttcgcttc aaaaaatgga ac                                           22

<210> SEQ ID NO 25
<211> LENGTH: 13
<212> TYPE: PRT
<213> ORGANISM: adeno-associated virus 1

<400> SEQUENCE: 25

Ser Arg Gly Ser Pro Ala Gly Met Ser Val Gln Pro Lys
1               5                   10

<210> SEQ ID NO 26
<211> LENGTH: 4
<212> TYPE: PRT
<213> ORGANISM: adeno-associated virus 1

<400> SEQUENCE: 26

Asn Phe Thr Trp
1

<210> SEQ ID NO 27
<211> LENGTH: 13
<212> TYPE: PRT
<213> ORGANISM: adeno-associated virus 3a

<400> SEQUENCE: 27

Ser Gln Ala Gly Pro Gln Ser Met Ser Leu Gln Ala Arg
1               5                   10

<210> SEQ ID NO 28
<211> LENGTH: 4
<212> TYPE: PRT
<213> ORGANISM: adeno-associated virus 3a

<400> SEQUENCE: 28

Asn Phe Pro Trp
1

<210> SEQ ID NO 29
<211> LENGTH: 4
<212> TYPE: PRT
<213> ORGANISM: Artificial
```

-continued

<220> FEATURE:
<223> OTHER INFORMATION: Insertion sequence for mutation of AAV4 to
graft galactose-binding footprint

<400> SEQUENCE: 29

Ser Ser Asn Asp
1

<210> SEQ ID NO 30
<211> LENGTH: 13
<212> TYPE: PRT
<213> ORGANISM: adeno-associated virus 4

<400> SEQUENCE: 30

Thr Lys Leu Arg Pro Thr Asn Phe Ser Asn Phe Lys Lys
1 5 10

<210> SEQ ID NO 31
<211> LENGTH: 4
<212> TYPE: PRT
<213> ORGANISM: adeno-associated virus 4

<400> SEQUENCE: 31

Asp Ser Leu Ile
1

<210> SEQ ID NO 32
<211> LENGTH: 13
<212> TYPE: PRT
<213> ORGANISM: adeno-associated virus 5

<400> SEQUENCE: 32

Asn Lys Asn Leu Ala Gly Arg Tyr Ala Asn Thr Tyr Lys
1 5 10

<210> SEQ ID NO 33
<211> LENGTH: 4
<212> TYPE: PRT
<213> ORGANISM: adeno-associated virus 5

<400> SEQUENCE: 33

Val Ser Ala Phe
1

<210> SEQ ID NO 34
<211> LENGTH: 13
<212> TYPE: PRT
<213> ORGANISM: adeno-associated virus 7

<400> SEQUENCE: 34

Val Gln Gly Gly Pro Ser Thr Met Ala Glu Gln Ala Lys
1 5 10

<210> SEQ ID NO 35
<211> LENGTH: 4
<212> TYPE: PRT
<213> ORGANISM: adeno-associated virus 7

<400> SEQUENCE: 35

Asn Phe Ala Trp
1

```
<210> SEQ ID NO 36
<211> LENGTH: 13
<212> TYPE: PRT
<213> ORGANISM: adeno-associated virus 8

<400> SEQUENCE: 36

Ser Gln Gly Gly Pro Asn Thr Asn Ala Asn Gln Ala Lys
1               5                   10

<210> SEQ ID NO 37
<211> LENGTH: 13
<212> TYPE: PRT
<213> ORGANISM: adeno-associated virus 10

<400> SEQUENCE: 37

Ser Gln Ala Gly Pro Ala Asn Met Ser Ala Gln Ala Lys
1               5                   10

<210> SEQ ID NO 38
<211> LENGTH: 13
<212> TYPE: PRT
<213> ORGANISM: Avian adeno-associated virus ATCC VR-865

<400> SEQUENCE: 38

Ser Arg Ala Thr Lys Thr Asn Met Ala Ala Gln Tyr Arg
1               5                   10

<210> SEQ ID NO 39
<211> LENGTH: 4
<212> TYPE: PRT
<213> ORGANISM: Avian adeno-associated virus ATCC VR-865

<400> SEQUENCE: 39

Phe Ser Val Trp
1

<210> SEQ ID NO 40
<211> LENGTH: 13
<212> TYPE: PRT
<213> ORGANISM: Non-human primate adeno-associated virus

<400> SEQUENCE: 40

Ser Gln Ala Gly Pro Asn Asn Met Ser Ala Gln Ala Arg
1               5                   10

<210> SEQ ID NO 41
<211> LENGTH: 13
<212> TYPE: PRT
<213> ORGANISM: Non-human primate adeno-associated virus

<400> SEQUENCE: 41

Ser Gln Ala Gly Pro Ser Ser Met Ala Gln Gln Ala Lys
1               5                   10

<210> SEQ ID NO 42
<211> LENGTH: 13
<212> TYPE: PRT
<213> ORGANISM: Non-human primate adeno-associated virus

<400> SEQUENCE: 42

Tyr Gln Gly Gly Pro Ser Thr Met Ala Glu Gln Ala Lys
1               5                   10
```

<210> SEQ ID NO 43
<211> LENGTH: 13
<212> TYPE: PRT
<213> ORGANISM: Non-human primate adeno-associated virus

<400> SEQUENCE: 43

His Gln Ala Gly Pro Asn Thr Met Ala Glu Gln Ser Lys
1               5                   10

<210> SEQ ID NO 44
<211> LENGTH: 13
<212> TYPE: PRT
<213> ORGANISM: Non-human primate adeno-associated virus

<400> SEQUENCE: 44

His Gln Ala Gly Pro Asn Thr Val Ala Glu Gln Ser Lys
1               5                   10

<210> SEQ ID NO 45
<211> LENGTH: 12
<212> TYPE: PRT
<213> ORGANISM: adeno-associated virus

<400> SEQUENCE: 45

Gln Ala Gly Ala Ser Asp Ile Arg Asp Gln Trp Arg
1               5                   10

<210> SEQ ID NO 46
<211> LENGTH: 12
<212> TYPE: PRT
<213> ORGANISM: adeno-associated virus 9

<400> SEQUENCE: 46

Val Ala Gly Pro Ser Asn Met Ala Val Gly Gln Arg
1               5                   10

<210> SEQ ID NO 47
<211> LENGTH: 12
<212> TYPE: PRT
<213> ORGANISM: adeno-associated virus

<400> SEQUENCE: 47

Gln Ala Gly Pro Thr Ser Met Ser Leu Gln Ala Lys
1               5                   10

<210> SEQ ID NO 48
<211> LENGTH: 12
<212> TYPE: PRT
<213> ORGANISM: adeno-associated virus

<400> SEQUENCE: 48

Gln Ala Gly Pro Thr Asn Met Ser Leu Gln Ala Lys
1               5                   10

<210> SEQ ID NO 49
<211> LENGTH: 12
<212> TYPE: PRT
<213> ORGANISM: adeno-associated virus 9

<400> SEQUENCE: 49

Val Ala Gly Pro Ser Asn Met Ala Val Gln Gly Arg
1               5                   10

```
<210> SEQ ID NO 50
<211> LENGTH: 13
<212> TYPE: PRT
<213> ORGANISM: adeno-associated virus

<400> SEQUENCE: 50

Ser Gln Ala Gly Pro Asn Asn Met Ser Ala Gln Ala Lys
1               5                   10

<210> SEQ ID NO 51
<211> LENGTH: 12
<212> TYPE: PRT
<213> ORGANISM: adeno-associated virus

<400> SEQUENCE: 51

Gln Ala Gly Ala Ser Asp Ile Arg Asp Gln Ser Arg
1               5                   10

<210> SEQ ID NO 52
<211> LENGTH: 13
<212> TYPE: PRT
<213> ORGANISM: adeno-associated virus 9

<400> SEQUENCE: 52

Val Ala Gly Pro Ser Asn Met Ala Val Gly Gln Arg Asn
1               5                   10

<210> SEQ ID NO 53
<211> LENGTH: 12
<212> TYPE: PRT
<213> ORGANISM: adeno-associated virus

<400> SEQUENCE: 53

Gln Ala Gly Pro Asn Asn Met Ser Ala Gln Ala Lys
1               5                   10

<210> SEQ ID NO 54
<211> LENGTH: 12
<212> TYPE: PRT
<213> ORGANISM: adeno-associated virus

<400> SEQUENCE: 54

Gln Ala Gly Ala Ser Asp Val Arg Asp Gln Ser Arg
1               5                   10

<210> SEQ ID NO 55
<211> LENGTH: 12
<212> TYPE: PRT
<213> ORGANISM: adeno-associated virus

<400> SEQUENCE: 55

Gln Ala Gly Ala Ser Asp Ile Gln Asp Gln Ser Arg
1               5                   10

<210> SEQ ID NO 56
<211> LENGTH: 12
<212> TYPE: PRT
<213> ORGANISM: adeno-associated virus

<400> SEQUENCE: 56

Gln Ala Gly Pro Ala Asn Met Ser Ala Gln Ala Lys
1               5                   10
```

```
<210> SEQ ID NO 57
<211> LENGTH: 12
<212> TYPE: PRT
<213> ORGANISM: adeno-associated virus

<400> SEQUENCE: 57

Arg Ala Gly Pro Ser Asn Met Ser Ala Gln Ala Arg
1               5                   10

<210> SEQ ID NO 58
<211> LENGTH: 12
<212> TYPE: PRT
<213> ORGANISM: adeno-associated virus

<400> SEQUENCE: 58

Arg Gly Ser Pro Ala Gly Met Ser Val Gln Pro Lys
1               5                   10

<210> SEQ ID NO 59
<211> LENGTH: 13
<212> TYPE: PRT
<213> ORGANISM: adeno-associated virus

<400> SEQUENCE: 59

Ser Gln Ala Gly Pro Thr Met Asn Ser Leu Gln Ala Lys
1               5                   10

<210> SEQ ID NO 60
<211> LENGTH: 13
<212> TYPE: PRT
<213> ORGANISM: adeno-associated virus

<400> SEQUENCE: 60

Ser Gln Ala Gly Pro Ser Ser Met Ala Asn Gln Ala Arg
1               5                   10

<210> SEQ ID NO 61
<211> LENGTH: 13
<212> TYPE: PRT
<213> ORGANISM: Non-human primate adeno-associated virus

<400> SEQUENCE: 61

Tyr Gln Gly Gly Pro Thr Thr Met Ala Glu Gln Ala Lys
1               5                   10

<210> SEQ ID NO 62
<211> LENGTH: 13
<212> TYPE: PRT
<213> ORGANISM: Non-human primate adeno-associated virus

<400> SEQUENCE: 62

Gly Lys Ile Arg Ser Gly Asp Phe Ala Phe Tyr Arg Lys
1               5                   10

<210> SEQ ID NO 63
<211> LENGTH: 13
<212> TYPE: PRT
<213> ORGANISM: adeno-associated virus

<400> SEQUENCE: 63

Ser Gln Ala Gly Pro Ala Asn Met Ser Ala Arg Ala Lys
1               5                   10
```

```
<210> SEQ ID NO 64
<211> LENGTH: 13
<212> TYPE: PRT
<213> ORGANISM: adeno-associated virus

<400> SEQUENCE: 64

Ser Gln Ala Gly Pro Ser Asn Met Ser Ala Gln Ala Arg
1               5                   10

<210> SEQ ID NO 65
<211> LENGTH: 735
<212> TYPE: PRT
<213> ORGANISM: adeno-associated virus 2

<400> SEQUENCE: 65

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
                20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320
```

```
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
            405                 410                 415
Asp Val Pro Phe His Ser Ser Tyr Ala His Ser Gln Ser Leu Asp Arg
        420                 425                 430
Leu Met Asn Pro Leu Ile Asp Gln Tyr Leu Tyr Tyr Leu Ser Arg Thr
    435                 440                 445
Asn Thr Pro Ser Gly Thr Thr Thr Gln Ser Arg Leu Gln Phe Ser Gln
450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
            485                 490                 495
Asn Ser Glu Tyr Ser Trp Thr Gly Ala Thr Lys Tyr His Leu Asn Gly
        500                 505                 510
Arg Asp Ser Leu Val Asn Pro Gly Pro Ala Met Ala Ser His Lys Asp
    515                 520                 525
Asp Glu Glu Lys Phe Phe Pro Gln Ser Gly Val Leu Ile Phe Gly Lys
530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
            565                 570                 575
Gly Ser Val Ser Thr Asn Leu Gln Arg Gly Asn Arg Gln Ala Ala Thr
        580                 585                 590
Ala Asp Val Asn Thr Gln Gly Val Leu Pro Gly Met Val Trp Gln Asp
    595                 600                 605
Arg Asp Val Tyr Leu Gln Gly Pro Ile Trp Ala Lys Ile Pro His Thr
610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
            645                 650                 655
Pro Ser Thr Thr Phe Ser Ala Ala Lys Phe Ala Ser Phe Ile Thr Gln
        660                 665                 670
Tyr Ser Thr Gly Gln Val Ser Val Glu Ile Glu Trp Glu Leu Gln Lys
    675                 680                 685
Glu Asn Ser Lys Arg Trp Asn Pro Glu Ile Gln Tyr Thr Ser Asn Tyr
690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
            725                 730                 735
```

<210> SEQ ID NO 66
<211> LENGTH: 738
<212> TYPE: PRT
<213> ORGANISM: adeno-associated virus 8

<400> SEQUENCE: 66

| | | | | | | | | | | | | | | |
|---|---|---|---|---|---|---|---|---|---|---|---|---|---|---|
| Met | Ala | Ala | Asp | Gly | Tyr | Leu | Pro | Asp | Trp | Leu | Glu | Asp | Asn | Leu |
| 1 | | | | 5 | | | | | 10 | | | | | 15 |
| Ser Glu | Gly | Ile | Arg | Glu | Trp | Trp | Ala | Leu | Lys | Pro | Gly | Ala | Pro | Lys | Pro |
| | | | 20 | | | | | 25 | | | | | 30 | | |

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

```
Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
                500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
        530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```